(12) United States Patent
Connolly et al.

(10) Patent No.: US 12,226,176 B2
(45) Date of Patent: Feb. 18, 2025

(54) AUTOMATIC INSTRUMENT POSITION ADJUSTMENT

(71) Applicant: Auris Health, Inc., Santa Clara, CA (US)

(72) Inventors: Ryan Jeffrey Connolly, San Carlos, CA (US); Casey Teal Landey, San Francisco, CA (US); Chauncey F. Graetzel, Palo Alto, CA (US)

(73) Assignee: Auris Health, Inc., Santa Clara, CA (US)

( * ) Notice: Subject to any disclaimer, the term of this patent is extended or adjusted under 35 U.S.C. 154(b) by 89 days.

(21) Appl. No.: 18/076,224

(22) Filed: Dec. 6, 2022

(65) Prior Publication Data

US 2023/0094003 A1 Mar. 30, 2023

Related U.S. Application Data

(60) Division of application No. 16/408,329, filed on May 9, 2019, now Pat. No. 11,534,247, which is a
(Continued)

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00147* (2013.01); *A61B 1/00149* (2013.01);
(Continued)

(58) Field of Classification Search
CPC . A61B 34/30; A61B 1/00147; A61B 1/00149; A61B 1/0016; A61B 1/0051;
(Continued)

(56) References Cited

U.S. PATENT DOCUMENTS 4,644,237 A 2/1987 Frushour et al.
4,745,908 A 5/1988 Wardle
(Continued)

FOREIGN PATENT DOCUMENTS

CN 1511249 A 7/2004
CN 1846181 A 10/2006
(Continued)

OTHER PUBLICATIONS

EP Examination Report for Appl. No. 18824858.7, dated Aug. 7, 2023, 4 pages.
(Continued)

*Primary Examiner* — Jason Holloway
(74) *Attorney, Agent, or Firm* — Paradice & Li LLP

(57) ABSTRACT

Disclosed herein are systems and techniques for compensating for insertion of an instrument into a working channel of another instrument in a surgical system. According to one embodiment, a method of compensation includes: detecting insertion of an insertable instrument into a working channel of a flexible instrument; detecting, based on a data signal from at least one sensor, a position change of a distal portion of the flexible instrument from an initial position: generating a control signal based on the detected position change; and adjusting a tensioning of a pull wire based on the control signal to return the distal portion to the initial position.

20 Claims, 13 Drawing Sheets

Related U.S. Application Data continuation of application No. 16/018,644, filed on Jun. 26, 2018, now Pat. No. 10,299,870.

(60) Provisional application No. 62/526,008, filed on Jun. 28, 2017.

(51) Int. Cl.

| | | |
|---|---|---|
| *A61B 1/005* | (2006.01) | |
| *A61B 1/018* | (2006.01) | |
| *A61B 1/267* | (2006.01) | |
| *A61B 5/06* | (2006.01) | |
| *A61B 34/00* | (2016.01) | |
| *A61B 34/20* | (2016.01) | |
| *A61B 90/00* | (2016.01) | |
| *A61B 90/90* | (2016.01) | |
| *A61B 5/08* | (2006.01) | |
| *A61B 17/00* | (2006.01) | |
| *A61B 90/30* | (2016.01) | |
| *A61B 90/96* | (2016.01) | |
| *A61B 90/98* | (2016.01) | |

(52) U.S. Cl.
CPC .......... *A61B 1/0016* (2013.01); *A61B 1/0051* (2013.01); *A61B 1/018* (2013.01); *A61B 1/2676* (2013.01); *A61B 5/062* (2013.01); *A61B 5/067* (2013.01); *A61B 34/20* (2016.02); *A61B 34/71* (2016.02); *A61B 90/361* (2016.02); *A61B 90/90* (2016.02); *A61B 5/0803* (2013.01); *A61B 2017/00809* (2013.01); *A61B 2034/2048* (2016.02); *A61B 2034/2051* (2016.02); *A61B 2034/2059* (2016.02); *A61B 2034/2065* (2016.02); *A61B 34/25* (2016.02); *A61B 2090/309* (2016.02); *A61B 2090/3614* (2016.02); *A61B 2090/376* (2016.02); *A61B 90/39* (2016.02); *A61B 2090/3966* (2016.02); *A61B 90/96* (2016.02); *A61B 90/98* (2016.02)

(58) Field of Classification Search
CPC ......... A61B 1/018; A61B 5/062; A61B 5/067; A61B 34/20; A61B 34/71; A61B 34/25; A61B 90/39; A61B 90/98; A61B 2034/2048; A61B 2034/2051; A61B 90/60

See application file for complete search history.

(56) References Cited

U.S. PATENT DOCUMENTS

| | | | |
|---|---|---|---|
| 4,748,969 | A | 6/1988 | Wardle |
| 5,194,791 | A | 3/1993 | Cull |
| 5,251,611 | A | 10/1993 | Zehel et al. |
| 5,280,781 | A | 1/1994 | Oku |
| 5,408,263 | A | 4/1995 | Kikuchi et al. |
| 5,672,877 | A | 9/1997 | Liebig et al. |
| 5,893,045 | A | 4/1999 | Kusama et al. |
| 5,899,851 | A | 5/1999 | Koninckx |
| 6,004,016 | A | 12/1999 | Spector |
| 6,198,974 | B1 | 3/2001 | Webster, Jr. |
| 6,246,200 | B1 | 6/2001 | Blumenkranz et al. |
| 6,459,926 | B1 | 10/2002 | Nowlin et al. |
| 6,580,938 | B1 | 6/2003 | Acker |
| 6,690,963 | B2 | 2/2004 | Ben-Haim et al. |
| 6,775,404 | B1 | 8/2004 | Pagoulatos et al. |
| 6,837,846 | B2 | 1/2005 | Jaffe et al. |
| 7,197,354 | B2 | 3/2007 | Sobe |
| 7,233,820 | B2 | 6/2007 | Gilboa |
| 7,607,440 | B2 | 10/2009 | Coste-Maniere et al. |
| 7,763,015 | B2 | 7/2010 | Cooper et al. |
| 7,772,541 | B2 | 8/2010 | Froggatt et al. |
| 7,901,348 | B2 | 3/2011 | Soper et al. |
| 7,963,288 | B2 | 6/2011 | Rosenberg et al. |
| 8,335,557 | B2 | 12/2012 | Maschke |
| 8,348,931 | B2 | 1/2013 | Cooper et al. |
| 8,376,934 | B2 | 2/2013 | Takahashi et al. |
| 8,396,595 | B2 | 3/2013 | Dariush |
| 8,442,618 | B2 | 5/2013 | Strommer et al. |
| 8,469,945 | B2 | 6/2013 | Schena |
| 8,498,691 | B2 | 7/2013 | Moll et al. |
| 8,506,555 | B2 | 8/2013 | Morales |
| 8,554,368 | B2 | 10/2013 | Fielding et al. |
| 8,720,448 | B2 | 5/2014 | Reis et al. |
| 8,738,181 | B2 | 5/2014 | Greer et al. |
| 8,801,601 | B2 | 8/2014 | Prisco et al. |
| 8,827,948 | B2 | 9/2014 | Romo et al. |
| 8,858,424 | B2 | 10/2014 | Hasegawa et al. |
| 8,894,610 | B2 | 11/2014 | MacNamara et al. |
| 8,929,631 | B2 | 1/2015 | Pfister et al. |
| 8,945,095 | B2 | 2/2015 | Blumenkranz et al. |
| 9,014,851 | B2 | 4/2015 | Wong et al. |
| 9,023,060 | B2 | 5/2015 | Cooper et al. |
| 9,129,417 | B2 | 9/2015 | Zheng et al. |
| 9,173,713 | B2 | 11/2015 | Hart et al. |
| 9,199,372 | B2 | 12/2015 | Henderson et al. |
| 9,226,796 | B2 | 1/2016 | Bowling et al. |
| 9,256,940 | B2 | 2/2016 | Carelsen et al. |
| 9,289,578 | B2 | 3/2016 | Walker et al. |
| 9,302,702 | B1 | 4/2016 | Schepmann et al. |
| 9,314,306 | B2 | 4/2016 | Yu |
| 9,345,456 | B2 | 5/2016 | Tsonton et al. |
| 9,358,682 | B2 | 6/2016 | Morales |
| 9,387,048 | B2 | 7/2016 | Donhowe et al. |
| 9,452,276 | B2 | 9/2016 | Duindam et al. |
| 9,504,604 | B2 | 11/2016 | Alvarez |
| 9,522,034 | B2 | 12/2016 | Johnson et al. |
| 9,561,083 | B2 | 2/2017 | Yu et al. |
| 9,622,827 | B2 | 4/2017 | Yu et al. |
| 9,629,595 | B2 | 4/2017 | Walker et al. |
| 9,636,184 | B2 | 5/2017 | Lee et al. |
| 9,675,422 | B2 | 6/2017 | Hourtash et al. |
| 9,713,509 | B2 | 7/2017 | Schuh et al. |
| 9,717,563 | B2 | 8/2017 | Tognaccini et al. |
| 9,726,476 | B2 | 8/2017 | Ramamurthy et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,789,608 | B2 | 10/2017 | Itkowitz et al. |
| 9,844,353 | B2 | 12/2017 | Walker et al. |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,046,140 | B2 | 8/2018 | Kokish et al. |
| 10,080,576 | B2 | 9/2018 | Romo et al. |
| 10,136,959 | B2 | 11/2018 | Mintz et al. |
| 10,143,526 | B2 | 12/2018 | Walker et al. |
| 10,145,747 | B1 | 12/2018 | Lin et al. |
| 10,149,720 | B2 | 12/2018 | Romo |
| 10,159,532 | B1 | 12/2018 | Ummalaneni |
| 10,159,533 | B2 | 12/2018 | Moll et al. |
| 10,169,875 | B2 | 1/2019 | Mintz et al. |
| 10,213,264 | B2 | 2/2019 | Tanner et al. |
| 10,219,874 | B2 | 3/2019 | Yu et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,285,574 | B2 | 5/2019 | Landey et al. |
| 10,454,347 | B2 | 10/2019 | Covington et al. |

(56) References Cited

U.S. PATENT DOCUMENTS

| | | | |
|---|---|---|---|
| 10,470,830 B2 | 11/2019 | Hill et al. |
| 10,482,599 B2 | 11/2019 | Mintz et al. |
| 10,517,692 B2 | 12/2019 | Eyre et al. |
| 10,524,866 B2 | 1/2020 | Srinivasan et al. |
| 2001/0000040 A1 | 3/2001 | Adams et al. |
| 2001/0021843 A1 | 9/2001 | Bosselmann et al. |
| 2002/0035330 A1 | 3/2002 | Cline et al. |
| 2002/0077533 A1 | 6/2002 | Bieger et al. |
| 2002/0161280 A1 | 10/2002 | Chatenever et al. |
| 2002/0173878 A1 | 11/2002 | Watanabe et al. |
| 2003/0045778 A1 | 3/2003 | Ohline et al. |
| 2003/0181809 A1 | 9/2003 | Hall et al. |
| 2003/0182091 A1 | 9/2003 | Kukuk |
| 2004/0257021 A1 | 12/2004 | Chang et al. |
| 2005/0043718 A1 | 2/2005 | Madhani et al. |
| 2005/0065400 A1 | 3/2005 | Banik et al. |
| 2005/0107917 A1 | 5/2005 | Smith et al. |
| 2005/0222554 A1 | 10/2005 | Wallace et al. |
| 2005/0234293 A1 | 10/2005 | Yamamoto et al. |
| 2005/0256398 A1 | 11/2005 | Hastings et al. |
| 2005/0261551 A1 | 11/2005 | Couvillon, Jr. et al. |
| 2005/0272975 A1 | 12/2005 | McWeeney et al. |
| 2006/0015096 A1 | 1/2006 | Hauck et al. |
| 2006/0041293 A1 | 2/2006 | Mehdizadeh et al. |
| 2006/0079745 A1 | 4/2006 | Viswanathan |
| 2006/0189891 A1 | 8/2006 | Waxman et al. |
| 2006/0200049 A1 | 9/2006 | Leo et al. |
| 2006/0258938 A1 | 11/2006 | Hoffman et al. |
| 2007/0013336 A1 | 1/2007 | Nowlin et al. |
| 2007/0043455 A1 | 2/2007 | Viswanathan et al. |
| 2007/0106147 A1 | 5/2007 | Altmann et al. |
| 2007/0135886 A1 | 6/2007 | Maschke |
| 2007/0142971 A1 | 6/2007 | Schena et al. |
| 2007/0150155 A1 | 6/2007 | Kawai et al. |
| 2007/0156019 A1 | 7/2007 | Larkin et al. |
| 2007/0249911 A1 | 10/2007 | Simon |
| 2007/0253599 A1 | 11/2007 | White et al. |
| 2007/0287992 A1 | 12/2007 | Diolaiti et al. |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0108870 A1 | 5/2008 | Wiita et al. |
| 2008/0123921 A1 | 5/2008 | Gielen et al. |
| 2008/0140087 A1 | 6/2008 | Barbagli |
| 2008/0159653 A1 | 7/2008 | Dunki-Jacobs et al. |
| 2008/0231221 A1 | 9/2008 | Ogawa |
| 2008/0249640 A1 | 10/2008 | Vittor et al. |
| 2008/0255505 A1 | 10/2008 | Carlson et al. |
| 2008/0312771 A1 | 12/2008 | Sugiura |
| 2009/0005768 A1 | 1/2009 | Sharareh et al. |
| 2009/0062813 A1 | 3/2009 | Prisco et al. |
| 2009/0076534 A1 | 3/2009 | Shelton et al. |
| 2009/0184825 A1 | 7/2009 | Anderson |
| 2009/0198298 A1 | 8/2009 | Kaiser et al. |
| 2009/0227861 A1 | 9/2009 | Ganatra et al. |
| 2009/0245600 A1 | 10/2009 | Hoffman et al. |
| 2009/0256905 A1 | 10/2009 | Tashiro |
| 2009/0287354 A1 | 11/2009 | Choi |
| 2009/0324161 A1 | 12/2009 | Prisco |
| 2010/0030061 A1 | 2/2010 | Canfield et al. |
| 2010/0030115 A1 | 2/2010 | Fujimoto et al. |
| 2010/0069920 A1 | 3/2010 | Naylor et al. |
| 2010/0076263 A1 | 3/2010 | Tanaka et al. |
| 2010/0121138 A1 | 5/2010 | Goldenberg et al. |
| 2010/0168918 A1 | 7/2010 | Zhao et al. |
| 2010/0204713 A1 | 8/2010 | Morales |
| 2010/0228266 A1 | 9/2010 | Hourtash |
| 2010/0234856 A1 | 9/2010 | Stoianovici et al. |
| 2010/0256812 A1 | 10/2010 | Tsusaka et al. |
| 2011/0009880 A1 | 1/2011 | Prisco et al. |
| 2011/0021926 A1 | 1/2011 | Spencer et al. |
| 2011/0082366 A1 | 4/2011 | Scully et al. |
| 2011/0082462 A1 | 4/2011 | Suarez et al. |
| 2011/0137122 A1 | 6/2011 | Kawai |
| 2011/0153252 A1 | 6/2011 | Govari et al. |
| 2011/0160570 A1 | 6/2011 | Kariv et al. |
| 2011/0196199 A1 | 8/2011 | Donhowe et al. |
| 2011/0218676 A1 | 9/2011 | Okazaki |
| 2011/0257480 A1 | 10/2011 | Takahashi et al. |
| 2011/0258842 A1 | 10/2011 | Dukesherer et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0069167 A1 | 3/2012 | Liu et al. |
| 2012/0071752 A1 | 3/2012 | Sewell et al. |
| 2012/0071822 A1 | 3/2012 | Romo et al. |
| 2012/0071894 A1 | 3/2012 | Tanner et al. |
| 2012/0123441 A1 | 5/2012 | Au et al. |
| 2012/0130217 A1 | 5/2012 | Kauphusman et al. |
| 2012/0209293 A1 | 8/2012 | Carlson et al. |
| 2012/0215094 A1 | 8/2012 | Rahimian et al. |
| 2012/0253276 A1 | 10/2012 | Govari et al. |
| 2012/0283745 A1 | 11/2012 | Goldberg et al. |
| 2012/0302869 A1 | 11/2012 | Koyrakh et al. |
| 2012/0328077 A1 | 12/2012 | Bouvier |
| 2013/0018306 A1 | 1/2013 | Ludwin |
| 2013/0085330 A1* | 4/2013 | Ramamurthy ......... A61B 34/77 600/117 |
| 2013/0090530 A1 | 4/2013 | Ramamurthy et al. |
| 2013/0096377 A1* | 4/2013 | Duindam ............... A61B 10/02 600/104 |
| 2013/0102846 A1 | 4/2013 | Sjostrom et al. |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle et al. |
| 2013/0218005 A1 | 8/2013 | Desai et al. |
| 2013/0303891 A1 | 11/2013 | Chopra et al. |
| 2013/0325030 A1 | 12/2013 | Hourtash et al. |
| 2014/0058428 A1 | 2/2014 | Christopher et al. |
| 2014/0114180 A1 | 4/2014 | Jain et al. |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0277333 A1 | 9/2014 | Lewis et al. |
| 2014/0296870 A1 | 10/2014 | Stern et al. |
| 2014/0316420 A1 | 10/2014 | Ballard et al. |
| 2014/0343569 A1 | 11/2014 | Turner |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0073267 A1 | 3/2015 | Brannan et al. |
| 2015/0088161 A1 | 3/2015 | Hata et al. |
| 2015/0104284 A1 | 4/2015 | Riedel et al. |
| 2015/0119628 A1 | 4/2015 | Bharat et al. |
| 2015/0119638 A1 | 4/2015 | Yu et al. |
| 2015/0150635 A1 | 6/2015 | Kilroy et al. |
| 2015/0164594 A1 | 6/2015 | Romo et al. |
| 2015/0164596 A1 | 6/2015 | Romo et al. |
| 2015/0202015 A1 | 7/2015 | Elhawary et al. |
| 2015/0223902 A1 | 8/2015 | Walker et al. |
| 2015/0265359 A1* | 9/2015 | Camarillo ......... A61M 25/0105 604/95.04 |
| 2015/0265368 A1 | 9/2015 | Chopra et al. |
| 2015/0265807 A1 | 9/2015 | Park et al. |
| 2015/0311838 A1 | 10/2015 | Moule et al. |
| 2015/0313503 A1 | 11/2015 | Seibel et al. |
| 2015/0335480 A1 | 11/2015 | Alvarez et al. |
| 2015/0342695 A1 | 12/2015 | He et al. |
| 2015/0359597 A1 | 12/2015 | Gombert et al. |
| 2015/0374956 A1 | 12/2015 | Bogusky |
| 2016/0000495 A1 | 1/2016 | Elliott et al. |
| 2016/0001038 A1 | 1/2016 | Romo et al. |
| 2016/0005168 A1 | 1/2016 | Merlet |
| 2016/0005220 A1 | 1/2016 | Weingarten et al. |
| 2016/0005576 A1 | 1/2016 | Tsukamoto |
| 2016/0016319 A1 | 1/2016 | Remirez et al. |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper et al. |

(56) References Cited

U.S. PATENT DOCUMENTS

| | | |
|---|---|---|
| 2016/0075030 A1 | 3/2016 | Takahashi et al. |
| 2016/0081568 A1 | 3/2016 | Kolberg et al. |
| 2016/0100772 A1 | 4/2016 | Ikuma et al. |
| 2016/0128992 A1 | 5/2016 | Hudson et al. |
| 2016/0183841 A1 | 6/2016 | Duindam et al. |
| 2016/0206389 A1 | 7/2016 | Miller et al. |
| 2016/0228032 A1 | 8/2016 | Walker et al. |
| 2016/0270865 A1 | 9/2016 | Landey et al. |
| 2016/0278865 A1 | 9/2016 | Capote et al. |
| 2016/0287053 A1 | 10/2016 | Miura et al. |
| 2016/0287111 A1 | 10/2016 | Jacobsen et al. |
| 2016/0287279 A1 | 10/2016 | Bovay et al. |
| 2016/0287346 A1 | 10/2016 | Hyodo et al. |
| 2016/0331469 A1 | 11/2016 | Hall et al. |
| 2016/0338787 A1 | 11/2016 | Popovic et al. |
| 2016/0346038 A1 | 12/2016 | Helgeson et al. |
| 2016/0346924 A1 | 12/2016 | Hasegawa et al. |
| 2016/0354057 A1 | 12/2016 | Hansen et al. |
| 2016/0360947 A1 | 12/2016 | Iida et al. |
| 2016/0360949 A1 | 12/2016 | Hyodo et al. |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0068796 A1 | 3/2017 | Passerini et al. |
| 2017/0084027 A1 | 3/2017 | Mintz et al. |
| 2017/0084927 A1 | 3/2017 | Banham et al. |
| 2017/0100197 A1 | 4/2017 | Zubiate et al. |
| 2017/0100199 A1 | 4/2017 | Yu et al. |
| 2017/0106904 A1 | 4/2017 | Hanson et al. |
| 2017/0119411 A1 | 5/2017 | Shah |
| 2017/0119481 A1 | 5/2017 | Romo et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0189118 A1 | 7/2017 | Chopra et al. |
| 2017/0202627 A1 | 7/2017 | Sramek et al. |
| 2017/0209073 A1 | 7/2017 | Sramek et al. |
| 2017/0245854 A1 | 8/2017 | Zemlok et al. |
| 2017/0245885 A1 | 8/2017 | Lenker |
| 2017/0251988 A1 | 9/2017 | Weber et al. |
| 2017/0280978 A1 | 10/2017 | Yamamoto et al. |
| 2017/0281049 A1 | 10/2017 | Yamamoto et al. |
| 2017/0290631 A1 | 10/2017 | Lee et al. |
| 2017/0303889 A1 | 10/2017 | Grim et al. |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0064498 A1 | 3/2018 | Kapadia et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0250085 A1 | 9/2018 | Simi et al. |
| 2018/0271604 A1 | 9/2018 | Grout et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Andey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167366 A1 | 6/2019 | Ummalaneni et al. |
| 2019/0167367 A1 | 6/2019 | Walker et al. |
| 2019/0175009 A1 | 6/2019 | Mintz et al. |
| 2019/0175062 A1 | 6/2019 | Rafii-Tari et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0209252 A1 | 7/2019 | Walker et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0246882 A1 | 8/2019 | Graetzel et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0008874 A1 | 1/2020 | Barbagli et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |

FOREIGN PATENT DOCUMENTS

| | | |
|---|---|---|
| CN | 1857877 A | 11/2006 |
| CN | 101325920 A | 12/2008 |
| CN | 102316817 A | 1/2012 |
| CN | 102458295 A | 5/2012 |
| CN | 102711586 A | 10/2012 |
| CN | 102973317 A | 3/2013 |
| CN | 103565529 A | 2/2014 |
| CN | 103735313 A | 4/2014 |
| CN | 103767659 A | 5/2014 |
| CN | 103874525 A | 6/2014 |
| CN | 103930063 A | 7/2014 |
| CN | 105559850 A | 5/2016 |
| CN | 105559886 A | 5/2016 |
| CN | 104931059 B | 9/2018 |
| DE | 102013100605 A1 | 7/2014 |
| EP | 1250986 A2 | 10/2002 |
| EP | 1566150 A2 | 8/2005 |
| EP | 1800593 A1 | 6/2007 |
| EP | 2158834 A1 | 3/2010 |
| EP | 2392435 A2 | 12/2011 |
| EP | 3025630 A1 | 6/2016 |
| JP | 2008071072 A | 3/2008 |
| JP | 2008528130 A | 7/2008 |
| JP | 2009509654 A | 3/2009 |
| JP | 2009524530 A | 7/2009 |

(56) References Cited

FOREIGN PATENT DOCUMENTS

| | | | |
|---|---|---|---|
| JP | 2011088260 A | 5/2011 | |
| JP | 2013510662 A | 3/2013 | |
| JP | 2014533996 A | 12/2014 | |
| JP | 2015519131 A | 7/2015 | |
| JP | 2017502709 A | 1/2017 | |
| RU | 2569699 C2 | 11/2015 | |
| WO | 1991009375 A1 | 6/1991 | |
| WO | 0156457 A1 | 8/2001 | |
| WO | 2004029782 A2 | 4/2004 | |
| WO | 2005087128 A1 | 9/2005 | |
| WO | 2006122061 A1 | 11/2006 | |
| WO | 2008111070 A2 | 9/2008 | |
| WO | 2009120940 A2 | 10/2009 | |
| WO | 2008065600 A3 | 11/2009 | |
| WO | 2009148317 A1 | 12/2009 | |
| WO | 2011132409 A1 | 10/2011 | |
| WO | 2012044334 A2 | 4/2012 | |
| WO | 2013056006 A2 | 4/2013 | |
| WO | 2014114551 A1 | 7/2014 | |
| WO | 2015061756 A1 | 4/2015 | |
| WO | 2015142957 A1 | 9/2015 | |
| WO | 201748194 | 3/2017 | |
| WO | 2017048194 A1 | 3/2017 | |
| WO | 2017049163 A1 | 3/2017 | |
| WO | 2017048194 A9 | 7/2017 | |

OTHER PUBLICATIONS

AU examination report for appl No. 2018290831, dated Jul. 12, 2021, 4 pages.
AU Examination Report for Appl. No. 2021204979, dated Apr. 13, 2022, 4 pages.
Blankenstein, Jun. 2008, Dynamic Registration and High Speed Visual Servoing in Robot-Assisted Surgery, Katholieke Universiteit Leuven, Leuven, Belgium, 96 pages.
CN office action for appl No. 201880043003, dated Apr. 13, 2021, 11 pages.
Devin V. Amin et al., Ultrasound Registration of the Bone Surface for Surgical Navigation, Computer Aided Surgery, 8:1-16, 2003, 17 pages.
EP Examination Report for Appl. No. 18824858.7, dated Nov. 25, 2022, 5 pages.
EP search report for appl No. 18824858, dated Mar. 2, 2021, 10 pages.
Heinz-Theo Luebbers et al., Comparison of different registration methods for surgical navigation in cranio-maxillofacial surgery, Journal of Cranio-Maxillofacial Surgery, 36:109-116, 2008, 8 pages.
International Search Report and Written Opinion dated Sep. 14, 2018 in application No. PCT/US2018/039604, 6 pages.
Intuitive, System, Instruments, and Accessories User Manual, 91 pages.
Ion by Intuitive, available at https://www.intuitive.com/en-us/products-and-services/ion,last accessed Aug. 12, 2021, 5 pages.
Jeffrey H. Shuhaiber, Augmented Reality in Surgery, Archive of Surgery, 139:170-174, Feb. 2004, 5 pages.
JP office action dated Feb. 26, 2021 for Patent Appl 2019-571320, 9 pages.
KR office action for appl 1020207002273, dated Mar. 15, 2021, 5 pages.
Kukuk, Oct. 5, 2001, TBNA-protocols: Guiding TransBronchial Needle Aspirations Without a Computer in the Operating Room, MICCAI 2001, 2208:997-1006.
Lawton et al., 1999, Ribbons and groups: A thin rod theory for catheters and filaments, J. Phys. A., 1999, 32:1709-1735, 27 pages.
Matthias Baumhauer et al., Navigation in Endoscopic Soft Tissue Surgery—Perspectives and Limitations, Journal of Endourology, 22(4):1-15, 2008, 16 pages.
MicroBIRD Product Brochure, Ascension Technology Corporation, available at http://www.ascension-tech.com/products/microbird.php, Jun. 12, 2019, 3 pages.
Non Final Rejection for U.S. Appl. No. 16/408,329, dated Feb. 3, 2022, 8 pages.
Notice of Allowance for U.S. Appl. No. 16/018,644, dated Apr. 11, 2019, 4 pages.
Notice of Allowance for U.S. Appl. No. 16/018,644, dated Jan. 9, 2019, 7 pages.
Notice of Allowance for U.S. Appl. No. 16/408,329, dated Jun. 1, 2022, 2 pages.
Notice of Allowance for U.S. Appl. No. 16/408,329, dated May 13, 2022, 7 pages.
Notice of Allowance for U.S. Appl. No. 16/408,329, dated Sep. 1, 2022, 7 pages.
Office Action for appl No. 2019571320, dated Dec. 20, 2021, 3 pages.
Robert Galloway & Terry Peters, Chapter 1: Overview and History of Image-Guided Interventions; David Holmes III et al, Chapter 3: Visualization in Image-Guided Interventions; Ziv Yaniv, Chapter 6: Rigid Registration, in Image-Guided Interventions: Technology and Applications, Terry Peters & Kevin Cleary eds., 2008, 95 pages.
Sargent, Dusty & Chen, Chao-I & Wang, Yuanfang, Cross Modality Registration of Video and Magnetic Tracker Data for 3D Appearance and Structure Modeling. Proceedings of SPIE—The International Society for Optical Engineering, 2010, 8 pages.
Verdaasdonk et al., Jan. 23, 2012, Effect of Microsecond Pulse Length and Tip Shape on Explosive Bubble Formation of 2.78 μm Er,Cr;YSGG and 2.94 μm Er:YAG laser, Proceedings of SPIE, vol. 8221, 12, 1 pages.

* cited by examiner

AUTOMATIC INSTRUMENT POSITION ADJUSTMENT

CROSS-REFERENCE TO RELATED APPLICATIONS

This application is a divisional of U.S. application Ser. No. 16/408,329, filed May 9, 2019, which is a continuation of U.S. application Ser. No. 16/018,644, filed Jun. 26, 2018, which claims the benefit of U.S. Provisional Application No. 62/526,008, filed Jun. 28, 2017, each of which is hereby incorporated by reference in its entirety.

TECHNICAL FIELD

The present disclosure relates generally to medical devices, and more particularly to robotically assisted surgery.

BACKGROUND

Medical procedures such as endoscopy (e.g., bronchoscopy) may involve accessing and visualizing the inside of a patient's lumen (e.g., airways) for diagnostic and/or therapeutic purposes. During a procedure a flexible tubular tool such as, for example, an endoscope, may be inserted into the patient's body and an instrument can be passed through the endoscope to a tissue site identified for diagnosis and/or treatment. For example, the endoscope can have an interior lumen (e.g., "working channel") providing a pathway to the tissue site, wherein various tools/instruments can be inserted through the interior lumen to the tissue site. A robotic system may be used to control the insertion and/or manipulation of the endoscope and/or the tools/instruments during the procedure, and may comprise at least one robotic arm that includes a manipulator assembly configured to control the positioning of the endoscope and/or tools/instrument during the procedure.

SUMMARY

The systems, techniques and devices of this disclosure each have several innovative aspects, no single one of which is solely responsible for the desirable attributes disclosed herein.

Medical procedures may involve the manipulation of a flexible instrument positioned remotely from an operator. For example, imaging, biopsy sampling, delivery of therapeutics and/or surgery can be performed within a lumen or luminal network to a target position within the patient corresponding to a desired tissue site and inserting another instrument through a working channel of the flexible instrument to gain access to the desired tissue site.

One challenge associated with existing flexible instruments for surgical purposes is that advancing or extending an insertable instrument through the working channel of the flexible instrument can cause deflection of the flexible instrument such that its distal end is moved from a target position. As the result of such deflection, the distal end of the flexible instrument can be misaligned with the tissue site.

Accordingly, certain aspects of this disclosure relate to systems and techniques that facilitate preventing, minimizing, and/or compensating for deflection of the flexible instrument when another instrument is inserted through the working channel of the flexible instrument. Another aspect of this disclosure relates to relates to systems and techniques that facilitate preventing, minimizing, and/or compensating for deflection of such a flexible instrument regardless of the source of the deflection.

Accordingly, a first aspect of the disclosure relates to a robotic system. The robotic system includes a first instrument, and the first instrument includes a shaft with a proximal portion and a distal portion. The distal portion includes an articulable region and a distal end. The shaft includes a working channel extending therethrough. The robotic system also includes at least one pull wire and at least one sensor configured to detect a position of the distal end of the shaft. The robotic system also includes at least one computer-readable memory having stored thereon executable instructions and one or more processors in communication with the at least one computer-readable memory. The one or more processors are configured to execute the instructions. The instructions cause the system to detect, based on a data signal from the at least one sensor, a position change of the distal end of the shaft in response to insertion of a second instrument into the working channel of the shaft. The instructions further cause the system to generate at least one control signal based on the detected position change. The robotic system also includes a drive mechanism connected to the at least one pull wire at the proximal portion of the shaft. The drive mechanism is configured to adjust a tensioning of the at least one pull wire based on the at least one control signal. The adjusted tensioning facilitates returning the distal end of the shaft towards an initial position before the position change occurred.

The robotic system according to one embodiment may include one or more of the following features, in any combination: the drive mechanism is connected to an end effector of a robotic arm, the robotic arm and the drive mechanism are configured to navigate the distal portion of the shaft through a luminal network of a patient to a treatment site; an electromagnetic (EM) field generator, the at least one sensor includes a first set of one or more EM sensors at the distal end of the shaft, and the one or more processors are configured to execute the instructions to cause the system to calculate a first position of the first set of EM sensors within the EM field based on data from the first set of EM sensors and detect the positon change of the distal end of the shaft based on the calculated first position; the second instrument further includes a second set of one or more EM sensors at the distal end, and the one or more processors are configured to execute the instructions to cause the system to calculate a second position of the second set of EM sensors within the EM field based on data from the second set of EM sensors and generate the at least one control signal further based on the calculated second position; the at least one sensor includes a set of one or more inertial sensors at the distal end of the shaft, and the one or more processors are configured to execute the instructions to cause the system to calculate a first position of the set of one or more inertial sensors based on data from the set of one or more inertial sensors, and generate the at least one control signal further based on the calculated first position; the at least one sensor includes a set of one or more strain gauges, and the one or more processors are configured to execute the instructions to cause the system to calculate a first position of the distal end of the shaft based on data from the set of one or more strain gauges, and generate the at least one control signal further based on the calculated first position; the drive mechanism includes the set of one or more strain gauges; the first instrument includes a leader, and the at least one sensor includes a set of one or more cameras at the distal end of the leader; the instructions of the at least one control signal includes commands for the drive mechanism to increase the tension in one or more of the pull wires until the distal end of the shaft is returned to the initial position as measured by a data signal from the at least one sensor; the one or more processors are a part of a workstation that includes a user interface for controlling the system; at least one respiration sensor and the one or more processors are further configured to execute the instructions to cause the system to determine, based on data from the at least one respiration sensor, a respiration pattern of a patient during acquisition of the data signal from the at least one sensor, and distinguish the position change of the distal end of the shaft caused by the insertion of the second instrument into the working channel from a position change of the distal end of the shaft caused by the respiration pattern of the patient; the one or more processors are configured to execute the instructions to cause the system to detect an identifier on the second instrument, and generate the at least one control signal further based on the detected identifier; and/or the one or more processors are configured to execute the instructions to cause the system to detect the identifier based on reading a radio frequency identification tag of the second instrument.

Embodiments discussed herein may relate to robotic systems that include a first instrument. The first instrument includes a shaft that includes a proximal portion and a distal portion. The distal portion includes an articulable region. The shaft includes a working channel extending therethrough. The robotic system includes at least one pull wire. The robotic system includes at least one sensor configured to detect, in response to insertion of a second instrument into the working channel, a position of a distal end of the second instrument within the working channel. The robotic system includes at least one computer-readable memory having stored thereon executable instructions. The robotic system includes one or more processors in communication with the at least one computer-readable memory and configured to execute the instructions. The instructions cause the system to calculate, based on a data signal from the at least one sensor, the position of the distal end of the second instrument within the working channel. The instructions further cause the system to generate at least one control signal based on the calculated position. The robotic system includes a drive mechanism connected to the at least one pull wire at the proximal portion of the shaft. The drive mechanism may be configured to adjust a tensioning of the at least one pull wire based on the at least one control signal, and the adjusted tensioning facilitates maintaining a position of the distal portion of the shaft.

Embodiments discussed herein may include one or more of the following features, in any combination: the drive mechanism is configured to adjust the tensioning of the at least one pull wire as the distal end of the second instrument advances to a determinable position in relation to the articulable region; the drive mechanism is configured to adjust the tensioning of the at least one pull wire before the distal end of the second instrument advances to the determinable position; the drive mechanism is configured to adjust the tensioning of the at least one pull wire after the distal end of the second instrument advances to the determinable position; the one or more processors are configured to execute the instructions to cause the system to detect an identifier on the second instrument; and generate the at least one control signal further based on the detected identifier; the one or more processors are configured to execute the instructions to cause the system to determine at least one physical property of the second instrument based on the detected identifier, the at least one physical property of the second instrument includes a flexural rigidity value, and the one or more processors are configured to execute the instructions to cause the system to generate the at least one control signal further based on the flexural rigidity value; the one or more processors are configured to execute the instructions to cause the system to determine an articulation angle of an articulable region of the shaft, and the one or more processors are configured to execute the instructions to cause the system to generate the at least one control signal further based on the articulation angle; the one or more processors are configured to execute the instructions to cause the system to detect the identifier based on reading a radio-frequency identification (RFID) tag of the second instrument; and/or an EM field generator, the at least one sensor includes a set of one or more EM sensors at the distal end of the second instrument, and the one or more processors are configured to execute the instructions to cause the system to calculate a position of the set of EM sensors within the EM field based on data from the set of EM sensors and calculate the positon of the distal end of the second instrument within the working channel further based on the calculated position.

Portions of this disclosure may discuss embodiments of methods for controlling at least one pull wire of a first instrument. This method includes determining an initial position of the first instrument. The first instrument includes a shaft that includes proximal and distal portions. The first instrument also includes the distal portion that includes an articulable region and a distal end. The first instrument also includes the shaft with a working channel extending therethrough. The first instrument also includes at least one pull wire. The method also includes detecting, based on a data signal from at least one sensor, a position change of the distal end of the shaft in response to insertion of a second instrument into the working channel of the first instrument. The method also includes generating at least one control signal based on the detected position change of the distal end of the shaft. The method also includes adjusting a tensioning of the at least one pull wire based on the at least one control signal and the adjusted tensioning facilitates returning the distal end of the shaft to the initial position.

Robotic systems for controlling at least one pull wire may include one or more of the following features, in any combination: the at least one sensor includes a first set of one or more EM sensors at the distal end of the shaft, and the detecting of the position change of the distal end of the shaft is further based on receiving data from the first set of one or more EM sensors; the at least one sensor includes a set of one or more inertial sensors at the distal end of the shaft, the detecting of the position change of the distal end of the shaft is based on data from the set of one or more inertial sensors; the at least one sensor includes a set of one or more one or more strain gauges, and the detecting of the position change of the distal end of the shaft is based on data from the set of one or more strain gauges; the at least one sensor includes a set of one or more cameras at the distal end of the first instrument, the detecting of the position change of the distal end of the shaft is based on data from the set of one or more cameras; and/or determining, based on data from at least one respiration sensor, a respiration pattern of a patient during acquisition of the data signal from the at least one sensor, and distinguishing the position change of the distal end of the shaft caused by the insertion of the second instrument into the working channel from a position change of the distal end of the shaft caused by the respiration pattern of the patient.

Portions of this disclosure may discuss embodiments of methods for controlling at least one pull wire of a first instrument. Such methods may include detecting insertion of a second instrument into a working channel of the first instrument. The second instrument includes proximal and distal ends. The first instrument includes a shaft having proximal and distal portions with the distal portion having an articulable region. The first instrument also includes at least one pull wire. The method also includes calculating a position of the distal end of the second instrument within the articulable region. The method also includes generating at least one control signal based on the calculated position. The method also includes adjusting a tensioning of the at least one pull wire based on the at least one control signal, wherein the adjusted tensioning facilitates maintaining a position of the distal portion of the shaft.

The robotic system implementing methods for controlling at least one pull wire may include one or more of the following features, in any combination: adjusting the tensioning of the at least one pull wire as the distal end of the second instrument advances to a determinable position in relation to the articulable region; adjusting the tensioning of the at least one pull wire before the distal end of the second instrument advances to the determinable position; adjusting the tensioning of the at least one pull wire after the distal end of the second instrument advances to the determinable position; detecting an identifier on the second instrument, and generating the at least one control signal further based on the detected identifier; determining at least one physical property of the second instrument based on the detected identifier, wherein the at least one control signal is generated further based on the at least one physical property; the at least one physical property includes a flexural rigidity value of the second instrument; the detecting of the identifier includes reading an RFID tag of the second instrument; and/or the calculated position of the distal end of the second instrument within the articulable region is based on data from at least one EM sensor on the distal end of the first instrument.

Portions of this disclosure may discuss embodiments of non-transitory computer readable storage media. Non-transitory computer readable storage media may have stored thereon instructions. These instruction when executed, cause at least one computing device to at least, for a first instrument includes at least one pull wire, determine an initial position of a distal end of a first instrument. The instructions further cause at least one computing device to detect, based on a data signal from at least one sensor, a position change of the distal end of the first instrument in response to insertion of a second instrument into a working channel of the first instrument. The instructions further cause at least one computing device to generate at least one control signal based on the detected position change. The instructions further cause at least one computing device to adjust a tensioning of the at least one pull wire based on the at least one control signal, and the adjusted tensioning facilitates returning the distal end of the first instrument to the initial position before the position change occurred.

A non-transitory computer readable storage medium consistent with embodiments discussed herein may include one or more of the following features, in any combination: the at least one sensor includes a set of one or more EM sensors at the distal end of the first instrument, and the instructions, when executed, cause the at least one computing device to detect the position change of the distal end of the first instrument based on data from the set of one or more EM sensors; the at least one sensor includes a set of one or more inertial sensors at the distal end of the first instrument, and the instructions, when executed, cause the at least one computing device to detect the position change of the distal end of the first instrument based on data from the set of one or more inertial sensors; the at least one sensor includes a set of one or more strain gauges configured to measure tensioning of the at least one pull wire, and the instructions, when executed, cause the at least one computing device to detect the position change of the distal end of the first instrument based on data from the set of one or more strain gauges; the at least one sensor includes a set of one or more cameras at the distal end of the first instrument, and the instructions, when executed, cause the at least one computing device to detect the position change of the distal end of the first instrument based on data from the set of one or more cameras; and/or the instructions, when executed, cause the at least one computing device to determine, based on data from at least one respiration sensor, a respiration pattern of a patient during acquisition of the data signal from the at least one sensor, and distinguish the position change of the distal end of the first instrument caused by the insertion of the second instrument into the working channel from a position change of the distal end of the first instrument caused by the respiration pattern of the patient.

Portions of this disclosure may discuss embodiments of a non-transitory computer readable storage medium that store instructions for adjusting tensioning of pull wires. These instructions, when executed, cause at least one computing device to at least, for a first instrument includes at least one pull wire and an articulable region, detect insertion of a second instrument into a working channel of the first instrument. The instructions further cause at least one computing device to calculate a position of a distal end of the second instrument within the articulable region. The instructions further cause at least one computing device to generate at least one control signal based on the calculated position. The instructions further cause at least one computing device to adjust a tensioning of the at least one pull wire based on the at least one control signal, wherein the adjusted tensioning facilitates maintaining a position of the distal portion of the first instrument.

The non-transitory computer readable storage medium of the sixth aspect may include one or more of the following features, in any combination: adjust the tensioning of the at least one pull wire as the distal end of the second instrument advances to a determinable position in relation to the articulable region; adjust the tensioning of the at least one pull wire before the distal end of the second instrument advances to the determinable position; adjust the tensioning of the at least one pull wire after the distal end of the second instrument advances to the determinable position; detect an identifier on the second instrument and generate the at least one control signal further based on the detected identifier; determine at least one physical property of the second instrument based on the detected identifier, and the at least one control signal is generated further based on the at least one physical property; and/or the at least one physical property includes a flexural rigidity value of the second instrument.

DETAILED DESCRIPTION

Introduction

Figure 1:
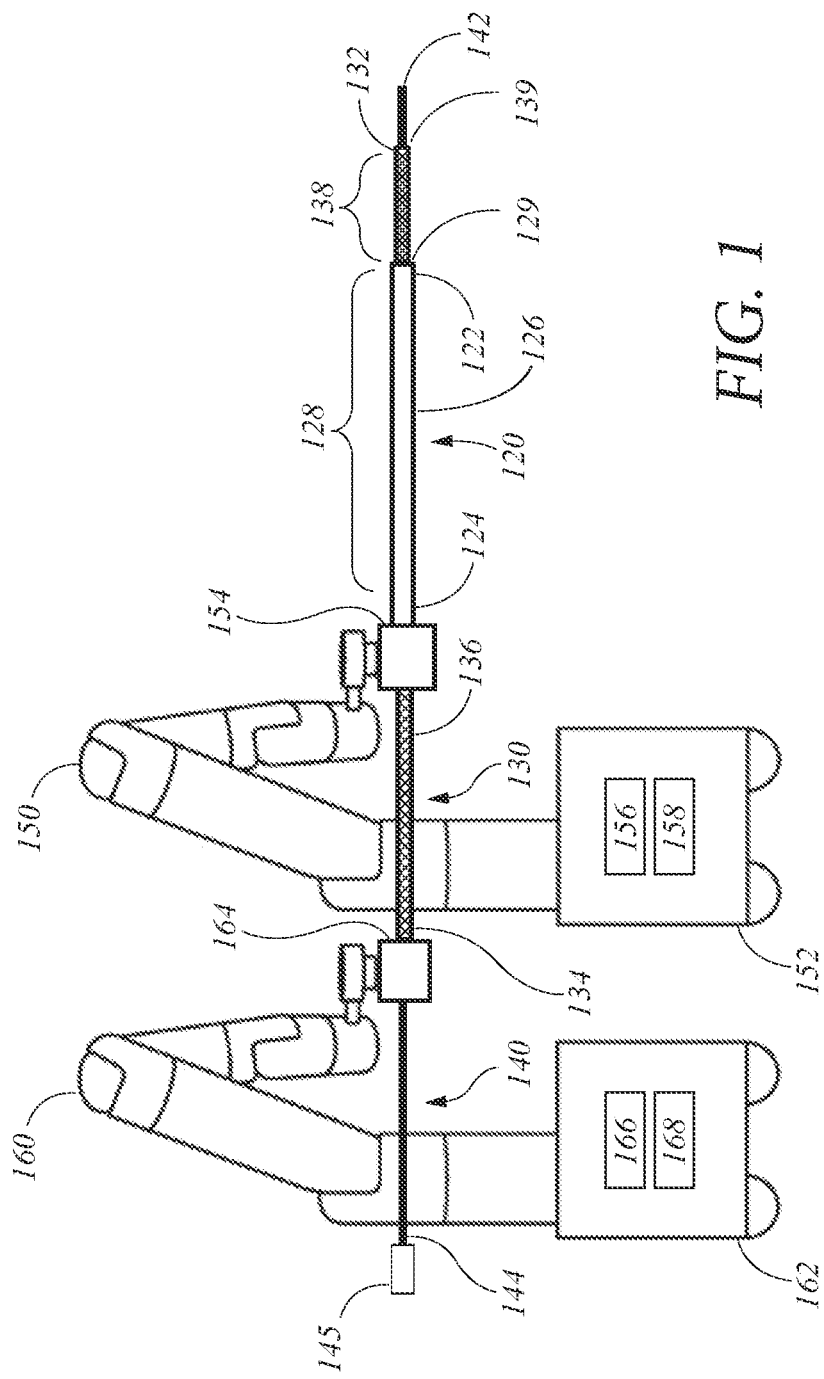
FIG. 1 illustrates an embodiment of a robotic system.

Medical procedures may involve the manipulation of an instrument positioned remotely from an operator. For example, imaging, biopsy sampling, delivery of therapeutics and/or surgery can be performed within a lumen or luminal network (e.g., lung, intestine, etc.) of the body by navigating a flexible instrument (e.g., trocars, catheters, endoscopes, etc.) to a target position within the patient corresponding to a desired tissue site and inserting another instrument through a working channel of the flexible instrument to gain access to the desired tissue site.

One example of a medical procedure performed with a flexible instrument is a minimally invasive bronchoscopic technique for diagnosis and staging of bronchial diseases called transbronchial needle aspiration (TBNA). A TBNA technique can involve manipulating a biopsy needle through the flexible instrument to take tissue samples at the tissue site within the lumen of the patient. For example, a physician can use chest scans to identify the location of a mass to be biopsied and to guide positioning of the flexible instrument within the patient's airways towards that mass. After a distal end of the flexible instrument is positioned within the lung near the identified mass, the biopsy needle can be advanced through the working channel of the flexible instrument to the location of the tissue. The tissue can then be pierced by extending the needle out of the working channel to puncture the tissue site with the needle. After sample acquisition, the needle can be retracted through the working channel.

One challenge associated with existing flexible instruments is that advancing or extending an insertable instrument through the working channel of the flexible instrument can cause deflection of the flexible instrument such that its distal end is deflected from a target position. The target position can be expressed, for example, at least in part as an articulation angle of the flexible instrument. By extending the insertable instrument through the working channel, the insertable instrument can cause a change in the articulation angle of the flexible instrument. As the result of such deflection, the distal end of the flexible instrument can be misaligned with the tissue site. Without detection by the physician, such deflection can result in medical procedures performed at the wrong location within the body. This is especially true where the tissue site, such as a lesion within a lung, has a small diameter. In some instances, manual correction for the deflection can be performed by a physician manipulating the flexible instrument back into the target position. This process, however, is time-consuming, especially in medical procedures that require the use of multiple instruments or checking of multiple tissue sites and can require further consultation of radiation-based navigational aids to guide the repositioning (e.g., fluoroscopy, x-rays, computerized axial tomography scanning, etc.).

Thus, one aspect of this disclosure relates to systems and techniques that facilitate preventing, minimizing, and/or compensating for deflection of the flexible instrument when another instrument is inserted through the working channel of the flexible instrument. Another aspect of this disclosure relates to relates to systems and techniques that facilitate preventing, minimizing, and/or compensating for deflection of such a flexible instrument regardless of the source of the deflection.

In some embodiments, a steerable endoscope may be used during a medical procedure. In one example, the endoscope may comprise at least two telescoping flexible instruments, such as an inner leader portion (referred to herein as the "leader") and an outer sheath portion (referred to herein as the "sheath").

As used herein, the terms "flexible instrument," "sheath," "leader." and "endoscope" can refer interchangeably to any type of flexible instrument that can inserted into the body of a patient for performing medical procedures. In some embodiments, but not all, the flexible instruments can include one or more cameras configured to facilitate navigation through an endoluminal pathway. These can include bronchoscopes, cystoscopes, endoscopes, colonoscopes, nephroscope, and other similar navigable instruments. Thus, although the embodiments disclosed below are present in the context of an endoscope or bronchoscope for insertion into a patient's lung, other applications for flexible instruments are contemplated herein. In some embodiments, the term "first instrument" can refer to the flexible instrument, endoscope, leader, or extended working channel thereof and the term "second instrument" can refer to an insertable instrument (e.g., an instrument that performs imaging, location detection, biopsy collection, delivery of therapeutics or surgery) that passes to the surgical site through the working channel of the first instrument.

As used herein, "distal" refers to the end of the scope or tool positioned closest to the patient tissue site during use, and "proximal" refers to the end of the instrument positioned closest to the operator (e.g., a physician or robotic control system). Stated differently, the relative positions of components of the robotic systems are described herein from the vantage point of the operator.

As used herein, the terms "about" or "approximately" refer to a range of measurements of a length, thickness, a quantity, time period, or other measurable values. Such range of measurements encompasses variations of +/−10% or less, preferably +/−5% or less, more preferably +/−1% or less, and still more preferably +/−0.1% or less, of and from the specified value, in so far as such variations are appropriate in order to function in the disclosed devices, systems, and techniques.

As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like.

Various embodiments will be described below in conjunction with the drawings for purposes of illustration. It should be appreciated that other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Example Robotic Systems

FIG. 1 illustrates an embodiment of a robotic system 100 configured to facilitate performing medical procedure(s) at a distance, such as within a lumen of a patient. The system 100 may comprise flexible instruments, such as a sheath 120 and a leader 130 through which an insertable instrument 140 can be inserted. As shown, with a sheath-and-leader arrangement of flexible instruments, the leader 130 and the sheath 120 are each coupled to a separate drive mechanism 154, 164, with each drive mechanism coupled to the distal end of a robotic arm 150, 160.

Figure 3:
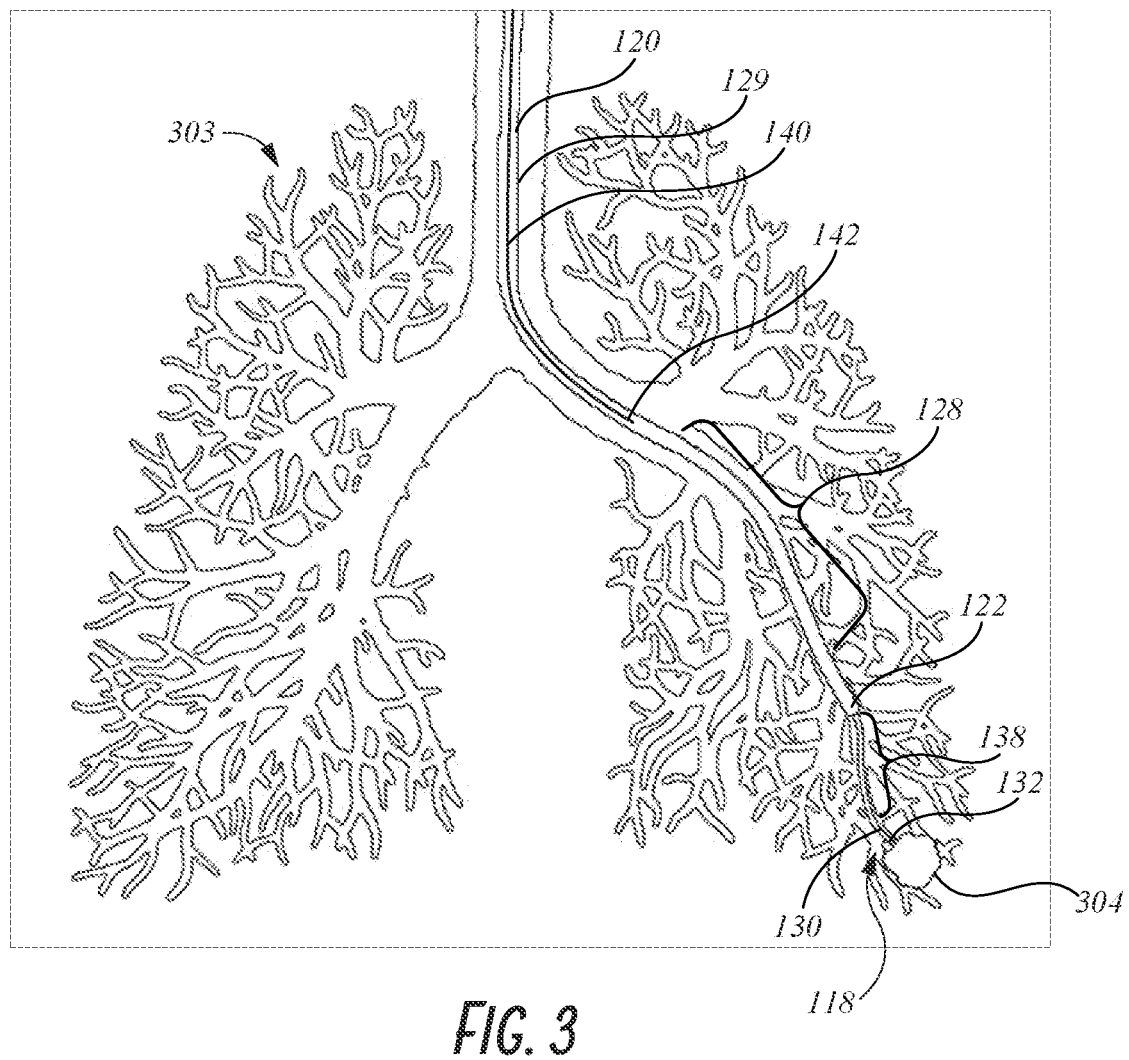
FIG. 3 illustrates the distal portion of robotic system within a luminal network.

The distal end 122 of the sheath 120 may be configured for insertion into a lumen of a patient (not shown) and the distal end 132 of the leader 130 can be inserted into a working channel 129 through the sheath 120 and navigated to a target position within the lumen of the patient, the target position corresponding to a tissue site of the lumen of the patient that is the target of the medical procedure(s) (see, e.g., FIG. 3). A distal end 142 of the insertable instrument 140 can be configured to be inserted through a working channel 139 of the leader 130 and advanced to the distal end 132 and thereby access the tissue site to perform the medical procedure(s).

The sheath 120 can include the distal end 122, a proximal end 124, a shaft 126 extending between the distal end 122 and the proximal end 124, and an articulable region 128 of the shaft 126. The articulable region 128 can be articulated with respect to a longitudinal axis of the shaft 126 to facilitate navigation of the sheath 120 through the lumen of the patient. The distal end 122 can be guided through the lumen of the patient by articulating the articulable region 128 (e.g., via the use of one more pull wires described in further detail below) to select a pathway for the distal end 122 and by advancing the shaft 126 and the distal end 122 through the lumen of the patient from the proximal end 124. In this manner, the distal end 122 can be navigated through the lumen of the patient to the tissue site. As noted above, various navigational aids and systems can support this process including but not limited to fluoroscopy, x-rays, and/or computerized axial tomography (CT) scanning. The articulable region 128 may be located between the proximal end 124 and the distal end 122, and is adjacent to the distal end 122 in the present example. This arrangement can facilitate the navigation of the sheath 120 through the luminal network of the patient.

The leader 130 can include the distal end 132, a proximal end 134, a shaft 136 extending between the distal end 132 and the proximal end 134, and an articulable region 138 of the shaft 136. The articulable region 138 can be articulated with respect to a longitudinal axis of the shaft 136 to facilitate navigation of the leader 130 through the lumen of the patient. The articulable region 138 may be located between the proximal end 134 and the distal end 132, and is adjacent to the distal end 132 in the present example. This arrangement can facilitate the navigation of the leader 130 through the luminal network of the patient.

As noted above, the distal end 132 of the leader 130 can be inserted into the proximal end 124 of the sheath 120 and supported, at least in part, thereby. The distal end 132 of the leader 130 can be extended out of the distal end 122 of the sheath 120 and guided through the lumen of the patient, e.g., by articulating the articulable region 138 (e.g., via the use of one more pull wires described in further detail below) to select a pathway for the distal end 132 and by advancing the leader 130 through the shaft 126 of the sheath 120. The sheath 120 can provide a base from which the leader 130 can be advanced and articulated to select the pathway through the lumen of the patient. The sheath 120 also can provide support and facilitate steering of the leader 130. Such an advancement technique can be used to advance the distal end 132 of the leader 130 through a luminal network of the patient to, e.g., reach a target position adjacent a tissue site. The advancement technique can be reversed to retract the leader 130 and the sheath 120 from the luminal network of the patient. In this manner, the distal end 132 of the leader 130 can be navigated through the lumen of the patient to/from the tissue site. As noted above, various navigational aids and systems can support this process including but not limited to fluoroscopy, x-rays, and/or CT scanning.

As shown in the example of FIG. 1, the proximal end 124 of the sheath 120 can be supported by a first robotic arm 150 configured to guide or navigate the sheath 120 through the lumen of the patient. The first robotic arm 150 can include a base 152 and multiple arm segments coupled at joints extending from the base, which gives the first robotic arm 150 multiple degrees of freedom. For example, one implementation of the first robotic arm 150 can have seven degrees of freedom corresponding to seven arm segments. In some embodiments, the first robotic arm 150 includes joints that use a combination of brakes and counter-balances to maintain a position of the first robotic arm 150. The counter-balances may include gas springs or coil springs. The brakes, e.g., fail safe brakes, may include mechanical and/or electrical components. Further, the first robotic arm 150 may be a gravity-assisted passive support type robotic arm.

An end effector may comprise a drive mechanism 154 coupled to the first robotic arm 150 and configured to control the sheath 120. The drive mechanism 154 can include connectors to transfer pneumatic pressure, electrical power, electrical signals, and/or optical signals from the first robotic arm 150 to the sheath 120. The drive mechanism 154 can be configured to manipulate the positioning of the sheath 120 using techniques including direct drive, harmonic drive, geared drives, belts and pulleys, magnetic drives, and/or the like. As described further below with reference to FIG. 5, the drive mechanism 154 can also be configured to manipulate the tensioning of pull wires to articulate the articulable region 128.

The base 152 of the first robotic arm 150 can include a source of power, pneumatic pressure, and control and sensor electronics—including components such as, for example, a central processing unit 156, data bus, control circuitry, and memory 158—and related actuators such as motors to move the first robotic arm 150. In some embodiments, the base 152 includes wheels to transport the robotic system 100 and wheel locks/brakes for the wheels. Mobility of the surgical robotic system 100 helps accommodate space constraints in a surgical operating room as well as facilitate appropriate positioning and movement of surgical equipment. Further, the mobility allows the first robotic arm 150 to be configured such that the first robotic arm 150 does not interfere with the patient, physician, anesthesiologist, or other equipment. During a medical procedure, a user may control the robotic arm 150 using control devices, for example, a command center (described in further detail below with reference to FIG. 7).

A proximal portion of the leader 130 (including a proximal end 134) can be supported by a second robotic arm 160 configured to guide the leader 130 through the working channel 129 of the sheath 120 and into/through the lumen of the patient. As with the first robotic arm 150, the second robotic arm 160 can include a base 162, multiple arm segments coupled at joints, brakes and/or counter-balances to maintain a position of the second robotic arm 160. As with the base 152 of the first robotic arm 150, the base 162 of the second robotic arm 160 can include a source of power, pneumatic pressure, and control and sensor electronics— including components such as, for example, a central processing unit 166, data bus, control circuitry, and memory 168—and related actuators such as motors to move the second robotic arm 160. In some embodiments, a base 162 of the second robotic arm includes wheels and locks/brakes for the wheels. In some embodiments of the robotic system 100, the first and second robotic arms 150, 160 can be mounted on the same base or mounted to the patient operating table.

An end effector or drive mechanism 164 (that may be similar to drive mechanism 154) can be coupled to the second robotic arm 160 and configured to control the leader 130. The drive mechanism 164 can include connectors to transfer pneumatic pressure, electrical power, electrical signals, and/or optical signals from the second robotic arm 160 to the leader 130. The drive mechanism 164 can be configured to manipulate the positioning of the leader 130 using techniques including direct drive, harmonic drive, geared drives, belts and pulleys, magnetic drives, and/or the like. As described further below with reference to FIG. 5, the drive mechanism 164 can also be configured to manipulate the tensioning of pull wires to articulate the articulable region 138.

The distal end 142 of the insertable instrument 140 can be configured to be inserted manually into the working channel 139 at the proximal end 134 of the leader 130. For example, a handle 145 on the distal end 144 of the insertable instrument 140 can be gripped by a user (e.g., a physician) and guided down the working channel 139 to the operating location. The handle 145 can include actuating mechanism(s) for operating the insertable instrument 140 to perform the desired medical procedure, such as a plunging or retraction motion for acquiring samples or therapeutics, as well as articulation for aiming or any other suitable motion. The distal end 142 of the insertable instrument 140 can be passed along the shafts 126, 136 and through the articulable regions 128, 138 to the distal end 132 of the leader 130. The passage of the distal end 142 of the insertable instrument 140 into the articulable region 138 of the leader 130 can cause an undesired deflection of the articulable region 138, as explained below with reference to FIG. 2B. Also, the passage of the distal end 142 into the articulable region 128 of the sheath 120 can cause an undesired deflection of the articulable region 128 of the sheath 120, similar to the deflection of the articulable region 138.

Figure 2A:
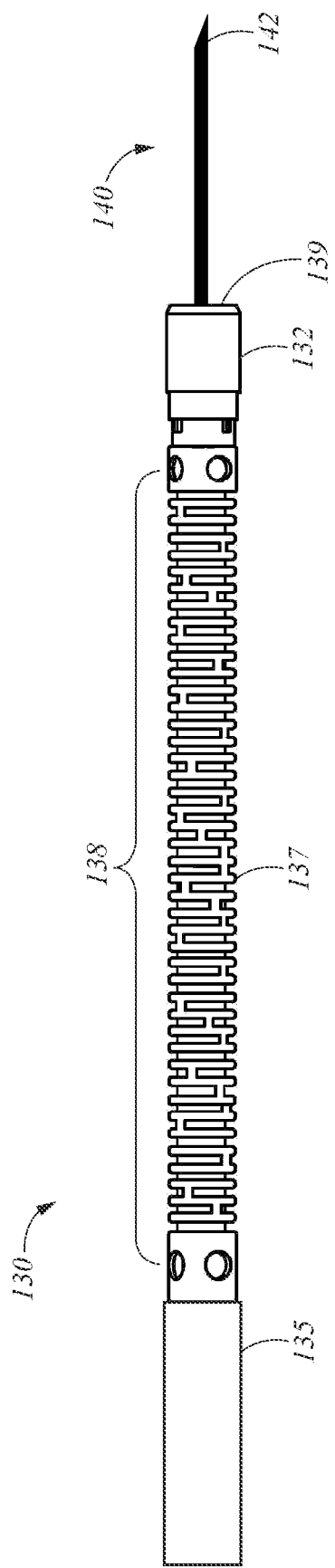
FIG. 2A illustrates a distal portion of the robotic system of FIG. 1.

As shown in the example of FIG. 2A, the articulable region 138 of shaft 136 is shown without being covered by an outer casing 135 for purposes of illustration. The outer casing 135 of the leader 130 can comprise a flexible polymer material (e.g., polyurethane or polyester elastomer, etc.) and provide protection against the entry of bodily fluids into the leader 130 and ensure a smooth interface with the lumen of the patient along the shaft 136. Furthermore, the outer casing 135 can be placed over a coiled metal band 137 that provides an outer structure to the shaft 136. Within the articulable region 138, the coiled metal band 137 can be structured such that the articulable region 138 is more flexible than the rest of the shaft 136, such as, for example, based on the spacing of the coils in the coiled metal band 137.

Figure 2B:
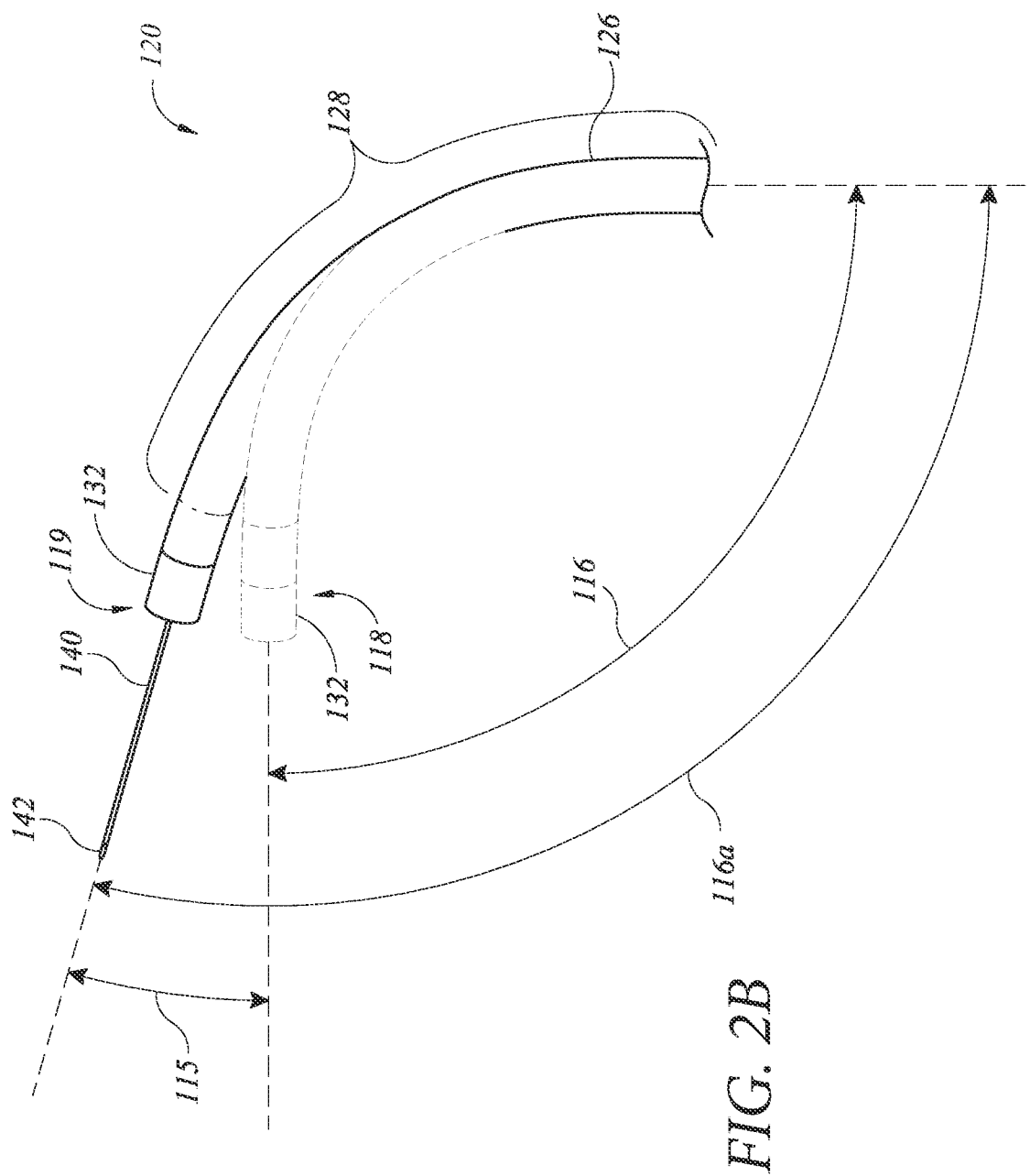
FIG. 2B illustrates deflection of the distal portion shown in FIG. 2A.

FIG. 2B illustrates an example of a distal portion of the robotic system 100 shown in FIG. 2A. As illustrated in broken lines, the distal end 132 is navigated to a target position 118 within the lumen of the patient, the target position 118 corresponding to a desired position of a distal portion (including the distal end 132) of the leader 130 within a defined distance of, and/or aligned with the tissue site that is the object of the medical procedure, such that the distal end 142 of the insertable instrument 140 can be extended from the distal end 132 of the leader 130 to access the tissue site. For example, the target position 118 can be at least partially expressed in terms of a location of the distal end 132 within the lumen of the patient (e.g., a position within a coordinate system), a navigational model of the lumen of the patient, the roll, pitch, and/or yaw of the distal end 132, and/or an articulation angle 116 of the articulable region 138.

As described above, the insertable instrument 140 can be advanced through the working channel 139 of the leader 130 to access the tissue site. Upon insertion of the distal end 142 of the insertable instrument 140 into the articulable region 138, the distal end 132 can be deflected or moved out of the target position 118, shown in dashed line, to a deflected position 119, shown in solid line. Similar to the target position 118, the deflected position 119 can be indicated by a change in the deflection angle 115 or by a new articulation angle 116a of the articulable region 138.

In one example, the deflected position 119 no longer corresponds with the tissue site, such that the extension of the distal end 142 of the insertable instrument 140 can be extended from the distal end 132 of the leader 130, but not have access to the tissue site, or be misaligned with the tissue site. In one illustrative example, during the collection of a tissue sample for a biopsy, the tissue site is a potentially cancerous lesion having a diameter less than about 3 cm. Insertion of a biopsy needle through the working channel can cause movement of the distal end 132 from the target position 118, thereby necessitating correction by the operator of the robotic system. Otherwise, the biopsy needle can miss the lesion and sample an incorrect tissue site within the lumen of the patient.

In another example, the deflection angle 115 can be as much as 15° or more, depending on a flexural rigidity of leader 130 and a flexural rigidity of the insertable instrument 140. Other factors that can influence the magnitude of the deflection angle 115 include the articulation angle 116, the diameters of the insertable instrument 140, or the flexural rigidity of the articulable region 138. Therefore, certain aspects of the systems and techniques described herein relate to deflection or movement of the distal portion of the leader 130 from the target position 118 and/or automatically preventing, minimizing, and/or compensating for the deflection.

In addition to deflection of the distal end 132 from the target position 118 due to insertion of the distal end 142 of the insertable instrument 140 into the articulable region 138, the distal end 132 can, in some embodiments, be deflected or moved out of the target position 118 by insertion of the distal end 142 through the articulable region 128 of the sheath 120. For example, an angle (not illustrated) of the articulable region 138 (similar to the deflection angle 115 of the articulable region 138) can be deflected of moved by insertion of the insertable instrument 140 into the working channel 129 and/or the articulable region 128. The distal end 132 can be deflected or moved, accordingly. This deflection or movement can be in addition to the deflection or movement from the change (if any) in the deflection angle 115 of the articulable region 138, as described above. Therefore, certain aspects of the systems and techniques described herein relate to detection of deflection of the distal portion of the leader 130 from the target position 118 due to deflection or movement of the sheath 120 and/or automatically preventing, minimizing, and/or compensating for the deflection or movement.

FIG. 3 illustrates the distal portion of the robotic system 100 within a luminal network or lumen 303 of a patient, for example a lung, as illustrated. The distal end 132 of the leader 130 can be navigated through the lumen 303 of the patient by advancing the proximal end 134, such as by the second robotic arm 160, and selecting a pathway through the lumen 303 of the patient with the distal end 132 by articulating the articulable region 138 with the drive mechanism 164. The shaft 136 of the leader 130 can be advanced through the working channel 129 of the sheath 120, such as by the second robotic arm 160, and the distal end 132 can be extended from the distal end 122 of the sheath 120. The shaft 126 and the distal end 122 of the sheath can be navigated through the lumen of the patient by being advanced along the shaft 136 of the leader 130. The sheath 120 can thereby provide a base from which the leader 130 can be again advanced through the lumen 303 and articulated to select the pathway through the lumen 303. The sheath 120 can also provide support and additional steering to the leader 130 by being articulated by the drive mechanism 154. This advancement technique can be repeated through the lumen 303 such that the distal end 132 of the leader 130 reaches the target position 118 adjacent a tissue site 304. The advancement technique can be reversed to retract the leader 130 and sheath 120 from the lumen 303.

The distal end 142 of the insertable instrument 140 can be advanced through the interior lumen 139 of the leader 130 and out of the distal end 132 (manually and/or robotically). The distal end of the insertable instrument 140 can thereby access the tissue site 304. As explained above with reference to FIG. 2B, the advancement of the insertable instrument 140 can cause a deflection of the articulable region 138 of the leader and/or the articulable region 128 of the sheath 120.

Accordingly, certain aspects of the systems and techniques described herein relate to detection of deflection of the distal end 132 of the leader 130 from the target position 118 and/or automatically preventing, minimizing, and/or compensating for the deflection. For example, it will be appreciated that the automatic nature in at least some of the embodiments described herein can provide substantial time savings over manual correction for deflection of the distal end 132 of the leader 130 (or the distal end 122 of the sheath 120). These time savings can facilitate faster recovery time for patients because of the reduced surgery time, reduced fatigue on physicians, surgeons and staff performing the medical procedures, less expensive medical procedures by reducing the amount of time necessary for completing the procedures and increasing the accuracy of said procedures and reduced error rate for performance of medical procedures because of the relative alertness of the physicians.

Another advantage of the present systems and techniques is improved accuracy for correcting a deflection. This improved accuracy can reduce the amount of time necessary for performing surgery by eliminating the need to repeat medical procedures that have been performed in the wrong location, lower the rate of false positives and false negatives for biopsies taken in the wrong location, reduce the number of procedures that need to be repeated for having been done incorrectly or in the wrong location and overall increase positive patient outcomes.

Another advantage of the present systems and techniques is improved detection of deflection. This improved detection rate can eliminate the need for repeat medical procedures that have been performed at the wrong location and thereby increase positive patient outcomes.

Figure 4A:
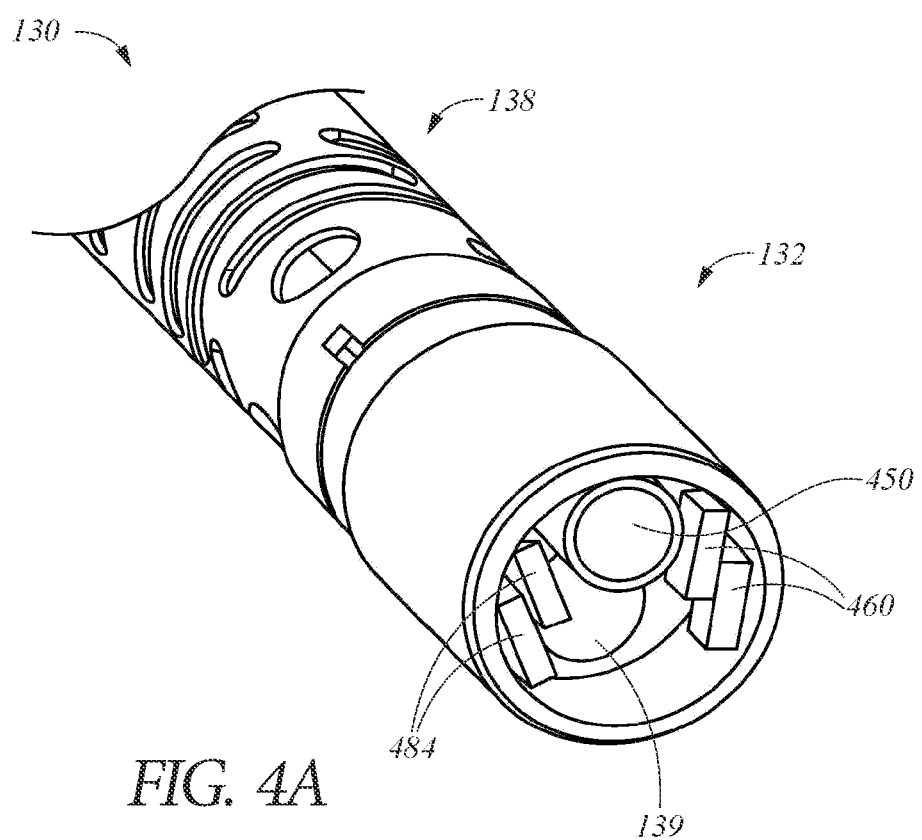
FIG. 4A illustrates a distal portion of an embodiment of a flexible instrument (e.g., a leader in a sheath-and-leader arrangement of flexible instruments).

FIG. 4A illustrates an embodiment of a distal portion of a flexible instrument, such as, for example, the leader 130. The distal portion can include the articulable region 138, the distal end 132, and a distal opening of the working channel 139. The distal portion of the leader 130 can further comprise tracking sensors for use in conjunction with one or more tracking systems or sensor modalities for locating a position of the distal end 132 of the leader 130. Further details regarding such tracking sensors and systems, in addition to the details herein, are described in U.S. application Ser. No. 15/268,238 filed on Sep. 17, 2016 and entitled "Navigation of Tubular Networks," the entirety of which is incorporated herein by reference.

Tracking systems that monitor these tracking sensors can be used to track and detect movement of the distal end 132, including movements such as those caused by insertion of the insertable instrument 140 into the working channel 139 or from other unwanted movements of the distal end. For example, a tracking system can detect whether the distal end 132 has been navigated by the system 100 into the target position 118, whether the distal end 132 has been deflected from the target position 118, and/or the magnitude of the deflection from the target position 118. Furthermore, each of the tracking systems can include or otherwise be in communication with a controller such as, for example, the command center 700 discussed below with reference to FIG. 7. The controller can include a processor communicatively coupled with a computer readable medium with instructions stored thereon for generating a control signal to the robotic system 100 for compensating for the measured or detected deflection of the distal end 132 from the target position 118 using the data from any of the tracking systems described below.

With continued reference to the example of FIG. 4A, a number of possible tracking systems are now discussed. In one example tracking system, the distal portion of the leader 130 can comprise one or more inertial sensors 460, such as an accelerometer and/or a gyroscope. The inertial sensor 460 can be configured to detect and/or measure changes in acceleration and output a data signal to a controller reflecting these measurements. In one embodiment, the inertial sensor 460 is a 3-axis microelectromechanical systems (MEMS)-based sensor chip with an accelerometer and can be coupled near distal end 132 of the leader 130, for example, on the same printed circuit board as a camera 450, as illustrated in FIG. 4, or on a different board. The accelerometer can measure a linear acceleration along the three different axes to calculate the velocity and direction of the distal end 132. Thus, movements of the distal end 132 out of the target position 118 can be detected and/or measured by the controller.

In one example, the inertial sensor 460 detects gravitational forces and provides information regarding the location of the endoscopic tool relative to the ground. If the inertial sensor 460 also measures the direction of gravity, the inertial sensor 460 can provide data containing absolute information about the orientation of the distal end 132 of the leader 130. In another example, if the leader 130 does not roll or bend up to ninety degrees, a two-axis accelerometer could also be used. In another example, a one-axis sensor can be useful if the axis of the accelerometer remains perpendicular to the direction of gravity, i.e., perpendicular to the ground. In yet another example, the inertial sensor 460 can comprise a gyroscope configured to measure the rate of rotation of the distal end 132, which can then be used to calculate the articulation of the leader 130.

The inertial sensor readings can be transmitted using digital or analog signals through a communication protocol to a controller. The signal can be transmitted through wiring to the proximal end of the catheter and from there to the controller for processing. Movements of the distal end 132 out of the target position 118 can be detected and/or measured by the controller.

As another example tracking system, the camera 450 can also be used as a part of an optical tracking system. The camera 450 in some embodiments is a charge coupling device (CCD), or fiber optic cable extending proximally to the distal end 132. Images from camera 450 can be ideal for navigating the distal end 132 of the leader 130 through anatomical spaces such as the lumen of the patient and arriving at the target position 118. The distal end 132 can also comprises a light source, such as an LED. In conjunction with the LEDs, the camera 450 can be used, for example, to capture real-time video to assist with navigation within a lumen of a patient. Internal bodily fluids, such as mucus, can cause problems when navigating. Accordingly, the distal end 132 can also include component(s) for cleaning the camera 450, such as component(s) for irrigation and/or aspiration of the camera lens.

In addition to navigation, the camera can be used to detect deflection of the distal end 132 and/or to measure the magnitude of such deflections. In the optical tracking system, an output or data signal from the camera 450 can be coupled with the controller whereby the data signal can be processed to detect and/or measure deflection of the distal end 132 out of the target position 118.

Figure 4B:
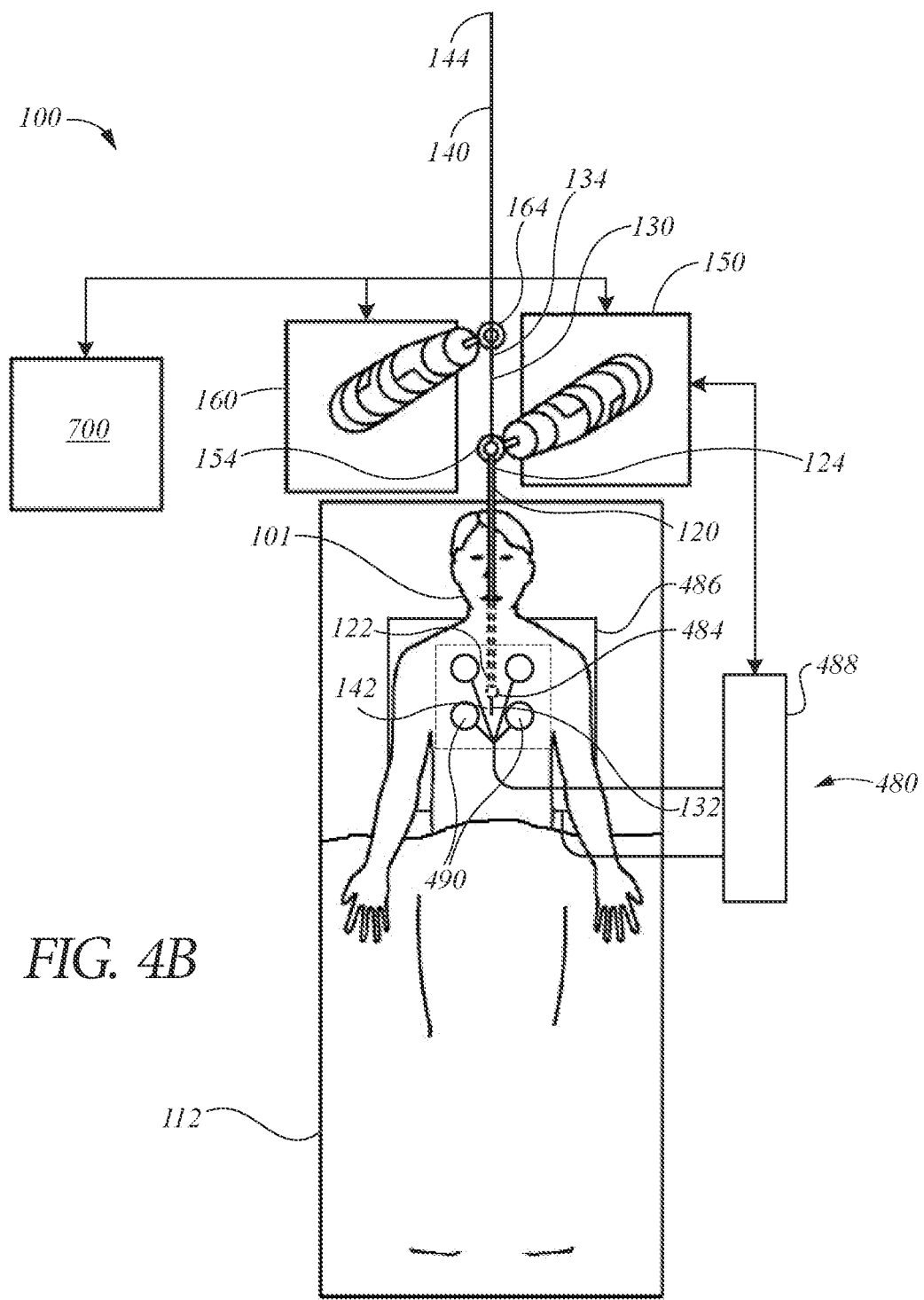
FIG. 4B illustrates a robotic system including an embodiment of an electromagnetic sensor system and a physiological sensor system.

The distal portion of the leader 130 can also comprise one or more electromagnetic (EM) trackers or sensors 484 on the distal end 132 and that may be used in conjunction with an EM tracking system 480 shown in FIG. 4B. The EM tracking system 480 can use the EM sensor 484 in conjunction with a generated electromagnetic field (EM field) to provide real-time indication of the position of the sensor within the electromagnetic field. Thus, a position of the distal end 122 can be tracked with an EM tracking system the distal end 132 includes one or more EM sensors 484. Moreover, any movements or deflection out of the target position 118 can be detected and/or the magnitude of the deflection measured using a data signal from the tracking system 480.

In EM-based tracking, a static EM field generator 486 generates an EM field. The EM field generator 486 can be placed close to a patient 101 to create a low intensity magnetic field. For example, as illustrated in FIG. 4B, the field generator 486 can be placed on a patient interface location 112 for supporting a body of the patient 101. For example, the patient interface location 112 can be a supporting platform for the patient 101 and the field generator can be placed under the patient. In another example, the field generator can be held on a robotic arm or placed around the sides of the patient interface location 112.

The static EM field generator 486 induces small-currents in sensor coils in the EM sensor 484, which are correlated to the distance and angle between the sensor and the generator. The electrical signal can then be digitized by an interface unit (on-chip or PCB) and sent via cables/wiring back to the system cart and then to the command center. The data can then be processed to interpret the current data and calculate the precise location and orientation of the EM sensor 484, relative to the transmitters or field generator 486. Multiple sensors can be used at different locations in the leader 130, for example, on the articulable region 138, to calculate the positions of those EM sensors as well.

Thus, based on readings from an artificially-generated EM field, the EM sensor 484 can detect changes in field strength as it moves through the patient's anatomy. A data signal from the EM sensor 484 can be transmitted down the shaft of the leader 130 to a controller 488 or alternatively, the controller or command center 700, for interpretation and analysis. Using the readings from EM sensor 484, display modules can display the EM sensor's relative position within a pre-generated three-dimensional model for review by the operator.

While a variety of sensors and tracking systems can be used for detecting and measuring deflection of the distal portion of the robotic systems 100 the choice of sensor(s) can be based at least in part on (i) the size of the sensor(s) within the endoscopic tool and (ii) the cost of manufacturing and integration the sensor(s) into the sheath 120.

A set of physiological sensors 490 can be used to track physiological movement of the patient. For example, the physiological sensors 490 can comprise one or more inertial sensors be positioned on the body of the patient to help estimate displacement of the chest surface during respiration. In another example, the physiological sensors 490 can comprise an EM patch or EM respiratory sensors configured to be placed on the body of the patient and used to measure the inspiration and expiration phases of the respiration cycle in conjunction with the EM tracking system 480. In another example, a number of additional EM patch sensors can be provided on the body of the patient (e.g., in the region of the lumen of the patient) in order to track displacement caused by respiration. In some embodiments, the data in the physiological sensors 490 can include, for each EM patch sensor, time-dependent position data representing the positions of the sensor in the EM field over time. A number of different EM patch sensors can be spaced apart on the body in order to track the different displacements at these locations. For example, the periphery of the lungs may exhibit greater motion due to respiration than the central airways, and providing a number of EM patch sensors can enable more precise analysis of these motion effects. Furthermore, the distal end 132 of the leader 130 travels through different regions of the lumen 303 and thus experiences varying levels of displacement due to patient respiration as it travels through these different regions. Data filtering techniques can correlate the approximate position of the distal end 132 of the leader 130 with one or more of the additional EM patch sensors, and can use identified displacement magnitudes of these specific additional EM patch sensors to correct for noise or artifacts in the endoscope position signal due to airway movement, for example, via filtering/removal of respiratory motion artifact component(s) of the endoscope position signal. This EM patch sensor embodiment of the physiological sensors 490 is further described in U.S. Provisional Application No. 62/480,257 filed on Mar. 31, 2017 and entitled "Robotic System for Navigation of Luminal Networks that Compensate for Physiological Noise," the entirety of which is incorporated herein by reference.

In another example, the physiological sensors 490 comprise an acoustic or other-type of respiratory sensor configured to be placed on the body of the patient in the region of the airways (e.g., lumen region 103) and used to measure the inspiration and expiration phases of the respiration cycle. In another example, the physiological sensors 490 can comprise an optical sensor (e.g., an imaging device) can capture a stream of images of the patient's body and these images can be analyzed to identify respiration phase and/or displacement. In some implementations, the patient 101 may be breathing with assistance from a ventilator during the procedure, and the ventilator (and/or a device communicatively coupled to the ventilator) may provide data representing inspiration and expiration phases of the respiration cycle.

Data from the physiological sensors can be used by the controller or command center 700 in conjunction with the data from the one or more tracking systems described above. By comparing this data from the physiological sensors, movements of the patient can be filtered out of the data from the tracking systems, such that the filtered data is indicative of movement of the distal end 132 of the leader 130 from deflection due to instrument insertion, rather than patient movement (e.g., during inspiration and expiration phases of the respiration cycle).

Figure 4C:
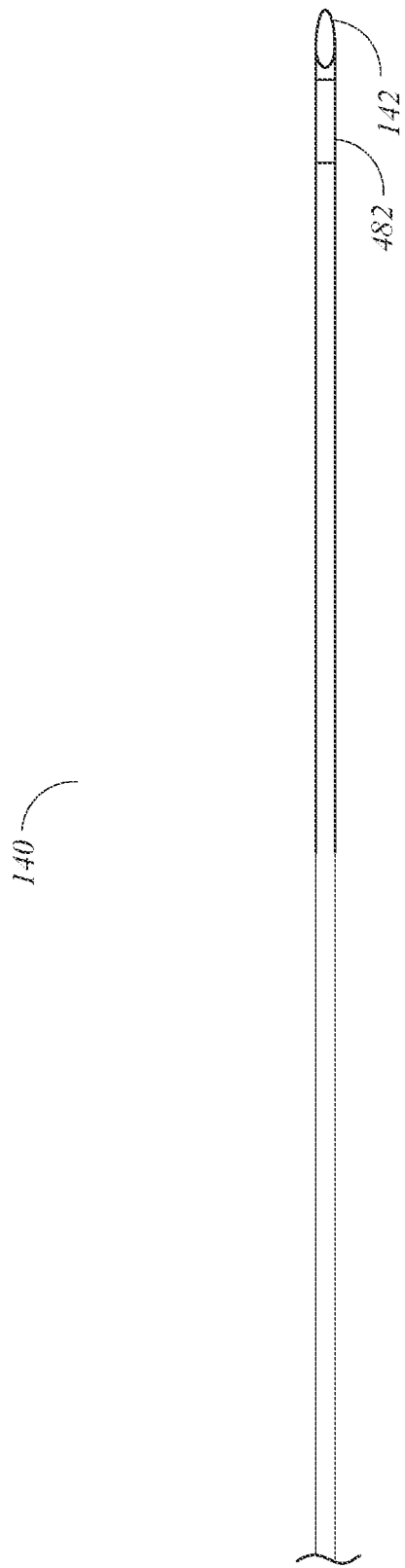
FIG. 4C illustrates a distal portion of an embodiment of an insertable instrument.

FIG. 4C depicts an embodiment of the insertable instrument 140 with an EM sensor 482 on the distal end 142 thereof. In some embodiments, such as in the robotic system 100 in which the insertable instrument 140 is inserted manually through the working channel 139 of the leader 130, the EM sensor 482 can be used in conjunction with the EM tracking system 480 to track the progress of the distal end 142 of the insertable instrument 140 through the leader 130 and/or within the lumen of the patient. Data from the EM sensor 482, such as data indicating the location of the distal end 142, can also be used in conjunction with any of the other tracking mechanisms described herein. For example, the data from the EM sensor 482 can be used to initialize or terminate any of the tracking systems described herein, for example, based on the location of the EM sensor within the leader 130 or its proximity to the distal end 132. In another example, the data from the sensor 482 can be used as a factor in timing adjustment of the articulable region 138, as described below in reference to FIGS. 5 and 9. In another example, the data from the sensor 482 can be used to calculate the distance of the distal end 142 from the articulable region 138 to know when the distal end 142 may be entering the articulable region 138. In another example, the data from the sensor 482 can be used to determine the trajectory of the distal end 142 to know when the distal end 142 may be entering the articulable region 138. In some embodiments, instead of or in addition to an EM-sensor 482, the insertable instrument 140 can comprise a metallic radioopaque band that can be tracked or seen using conventional radiation-based navigational aids (e.g., fluoroscopy, x-rays, computerized axial tomography scanning, etc.).

In some embodiments, the insertable instrument 140 can comprise an identification tag, the tag corresponding to or containing information about the specific insertable instrument 140, and including information such as, for example, the instrument's physical properties. In some embodiments, the robotic system 100 can automatically identify the insertable instrument 140 based on the tag. For example, the tag can be an RFID tag, barcode, or the like. In some embodiments, the physical properties associated with the insertable instrument 140 can be encoded into the identifier (e.g., RFID tag) and taken into account by the robotic system 100 to determine an expected deflection response of the leader 130 due to the insertion of the insertable instrument 140 into the working channel 139.

Figure 5:
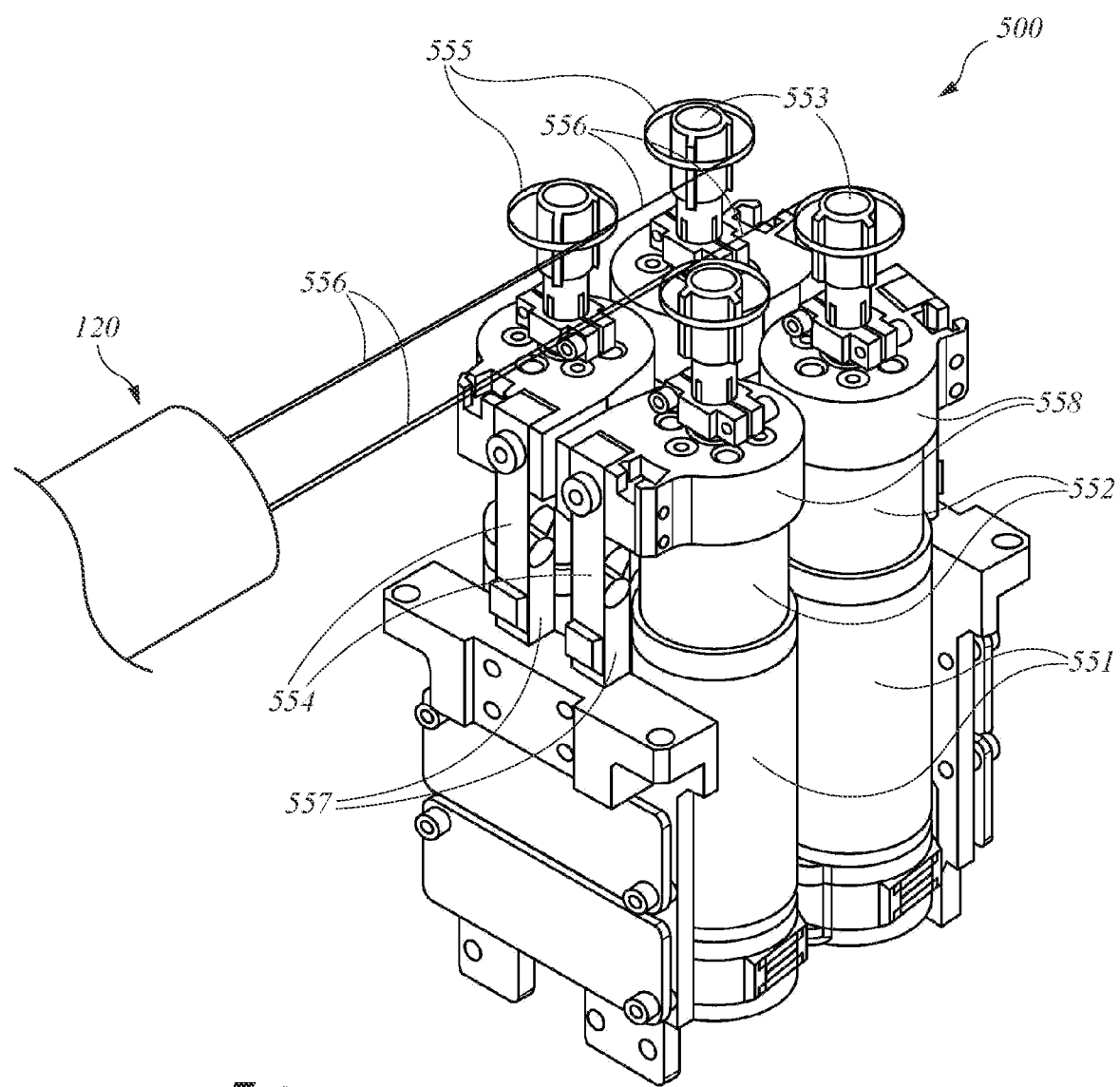
FIG. 5 illustrates an embodiment of a drive mechanism for controlling a flexible instrument.

FIG. 5 depicts an embodiment of a drive mechanism 500 configured to control one or more pull wires 556. For example, the drive mechanism 500 can correspond to one or more of the drive mechanisms 154 or 164, or other robotic systems described herein. Although described herein with reference to the leader 130, embodiments of the drive mechanism can also be used in conjunction with the sheath 120 or any other flexible instrument.

The drive mechanism 500 is configured to control one or more pull wires 556 for manipulating the leader 130 from the proximal end 134. By controlling the position of the distal end 132 the articulable region 138 and by advancing the shaft 136 of the leader 130 through the lumen of the patient, the leader 130 can be navigated to the target position 118, such as in response to physician inputs at a control center of the system 100. The pull wires 556 can control the articulation angle 116 and direction of the articulable region 138. Once the distal end 132 of the leader 130 is at the target position 118, in some embodiments, the pull wires 556 can be locked in place to maintain the distal end in a desired position or orientation, for example, corresponding to the target position 118 described above with reference to FIG. 2B. Locking the pull wires may involve increasing the tension on the pull wires 556 such that the force needed to move the leader 130 is increased.

The pull wires 556 can extend along a longitudinal length of the leader 130. In some embodiments, the pull wires 556 are attached distally within the leader 130 with respect to an articulable region of the leader 130. The pull wires can be arranged around a periphery of the shaft 136 of the leader 130 such that increasing the tension of one pull wire will tend to articulate the articulable region in the direction of that pull wire. For example, four pull wires can be spaced evenly around the shaft 136 with one pull wire in each cardinal direction.

The pull wires 556 can include both metallic and non-metallic materials such as, for example, stainless steel, Kevlar, tungsten, carbon fiber, and/or the like. The leader 130 may exhibit nonlinear behavior in response to forces applied by the pull wires. The nonlinear behavior may be based on stiffness and compressibility of the shaft 126 of the leader 130, as well as variability in slack or stiffness between different pull wires.

The drive mechanism 500 can include motors 551, each corresponding to and rotationally coupled with gear boxes 552. The pull wires 556 can be correspondingly coupled with shafts 553 extending from the gear boxes 552. The shafts 553 can be configured to apply a tensioning force on the pull wires 556 from rotation of the shafts 553 by rotation of the corresponding motors 551. The pull wires 556 can be connected with the shafts 553 through pulleys 555 configured to secure the ends of the pull wires with the shafts and apply a tensioning force along the pull wires through a rotational movement of the shafts 553. Alternatively, the pull wires 556 can be attached directly to the output shafts 553 with or without the pulleys 555.

As shown in the example of FIG. 5, the pulleys 555 can be longitudinally aligned and concentric with output shafts 553 of the motors 551. The splines of the pulleys 555 can be designed such that they align and lock with splines on output shaft 553. In some embodiments, the splines are designed such that there is a single orientation for the leader 130 to be aligned with drive mechanism 500. Locked into alignment, rotation of the shaft 553 and pulley 555 tensions the pull wires 556 within the leader 130, resulting in articulation of the articulable region 138 of the leader 130.

In some embodiments, the drive mechanism 500 can further comprise a controller or be communicatively coupled with an external controller (e.g., the command center 700 of FIG. 7 described in further detail below) for controlling the rotation of the motors 551 and tensioning of the pull wires 556. In some embodiments, the drive mechanism 500 includes rotational encoders coupled with the shafts 553 for measuring rotational position, speed, and or acceleration of the output shafts. In some embodiments, the controller is onboard the drive mechanism 500, within a housing of the drive mechanism or a robotic arm on which the drive mechanism 500 is mounted. The controller can be coupled with the motors 551 and configured with a processor for executing instructions stored on a computer readable medium to control the tensioning of one or more of the pull wires 556.

It is noted that the controller can include a processer thereon for executing instructions stored on a computer readable medium. The computer readable medium can have instructions stored thereon for generating a control signal to the robotic system for compensating for the measured or detected deflection of the distal end 132 from the target position 118 using the data from any of the tracking systems described above. For example, the instructions can cause the processor to process the data and generate a control signal to adjust the tensioning on specific pull wire(s) of the plurality of pull wires 556 using either or both of the drive mechanisms 154, 164.

In some embodiments the instructions of the control signal are executed by the driver 500 before the distal end 142 of the insertable instrument 140 is inserted through an articulable region 138. In such a preemptive model or approach, the distal end 132 may be deflected out of the target position 118 only to be returned to the target position 118 by adjusting the tensioning on the plurality of pull wires 556 when the instrument 140 is extended through the articulable region. In another example, the instructions of the control signal can be executed after the distal end 142 of the insertable instrument 140 is inserted through an articulable region 138. In such a model or approach, the distal end 132 is returned to the target position 118 after the instrument 140 is extended through the articulable region by adjusting the tensioning on the plurality of pull wires 556. In yet another embodiment, the instructions of control signal can be executed as the distal end 142 of the instrument 140 is inserted through the articulable region 138. Thus, the distal end 132 can be maintained substantially in the target position 118 during advancement of the insertable instrument 140 by adjusting the tensioning on the plurality of pull wires 556 in coordination with the advancement of the distal end 142. Any of these techniques can be performed in conjunction with data indicating the location of the distal end 142 of the insertable instrument 140, such as data from the EM sensor 182.

In one embodiment, the control signal can include instructions for the tension in one or more of the pull wires 556 to be gradually increased by the drive mechanism 500 until the distal end 132 is returned to the target position 118. For example, the tension can be increased until the arrival at the target position 118 as measured or tracked by the optical tracking system using the camera 450 to determine the position of the distal end 132. As another example, the tension can be increased until the arrival at the target position 118 as measured or tracked by the EM tracking system 480 or the inertial tracking system to determine the position of the distal end 132. In some cases, the tensioning of a pull wire can axially compress a flexible instrument, thereby shortening the distal length of the flexible instrument. In such cases, the control signal may compensate for this shortening by causing the flexible instrument to be inserted in the anatomy by a distance that corrects for the axial compression.

The drive mechanism 500 can include a tension sensing system for monitoring the movement and position of the distal portion of the leader 130. This tension sensing system can be configured to detect and/or measure a deflection or movement of a distal end 132 of the leader 130 by detecting change in the tensioning of the pull wires 556 caused by such deflection. For example, the drive mechanism 500 can monitor specific pull wires of the pull wires 556 to monitor these specific pull wires for an increase or decrease in tension.

For example, the drive mechanism 500 can comprises one or more electrical strain gauges 554 for detecting/measuring the deflection of the pull wire(s) 556 based on any measured changes in the tensioning of the pull wire(s) 556. For example, in certain embodiments, the strain gauges 554 are coupled between motor mounts 558 corresponding to each of the motors 551 and strain gauge mounts 557. Strain gauges 554 can be potted and soldered to the strain gauge mount 557 and attached using screws to motor mounts 558 respectively. The strain gauges 554 can be held in place to their respective motor mount using side screws. The gauge wiring in the strain gauges 554 can be vertically arranged to detect any vertical strain or flex in the drive mechanism which is measured as horizontal displacement by the motor mount 558 relative to the strain gauge mount 557. The amount of strain can be measured as a ratio of the horizontal displacement of the tip of strain gauge 554 to the overall horizontal width of the strain gauge 554. Accordingly, the strain gauge 554 can ultimately measure the force exerted on the shaft 553 by the pull wire 556.

The strain gauges 554 can be configured such that any change in the tensioning of any of the pull wires 556 can be detected and measured. The drive mechanism 500 can be calibrated such that the strain measured in the strain gauges 554 can be correlated to a position of the leader 130, such as the position of the distal end 132 and/or the deflection angle 116 of the articulable region 128. Any change in the position of the distal end 132 can thus be detected and/or measured.

Figure 7:
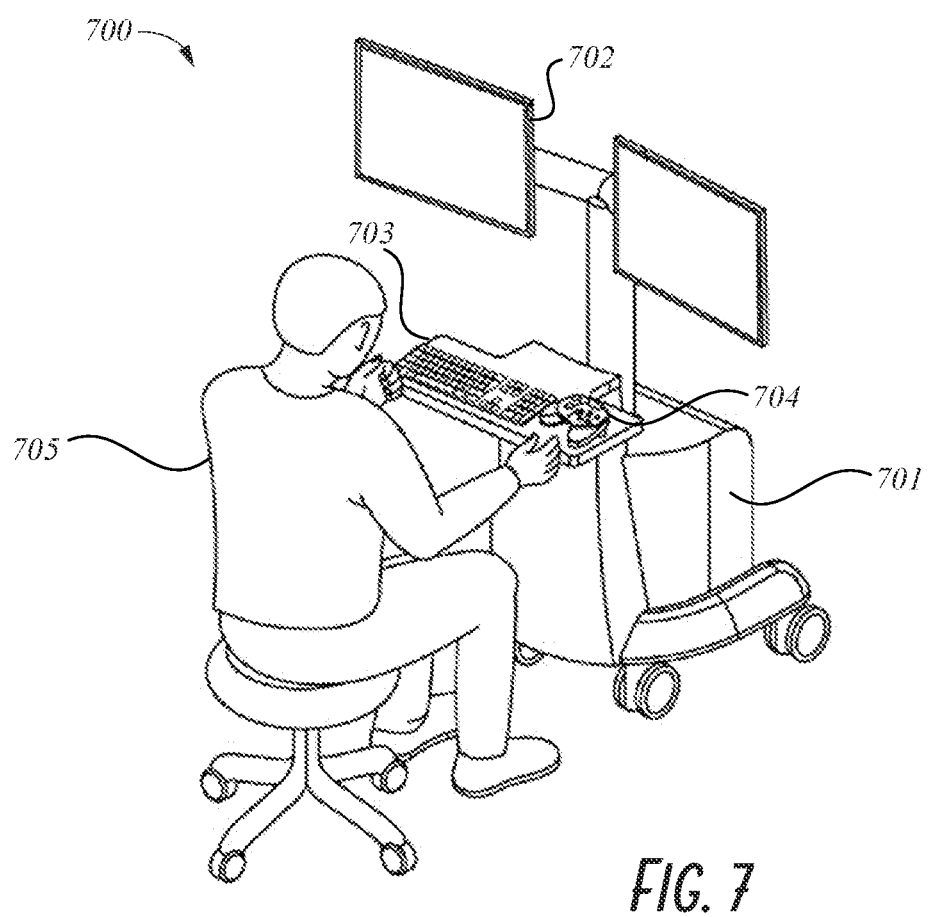
FIG. 7 illustrates an embodiment of a work station for use with a robotic system.

A data signal from the strain gauge 554 and/or from circuitry coupled with the strain gauge 554 can be delivered to a controller (e.g., within the drive mechanism 500 shown in FIG. 5 or the command center 700 in FIG. 7). This data signal can contain data indicating the changes in the tensioning of the pull wire(s) 556, the movement of the pull wire(s) 556 and/or the movement of the sheath 120. Accordingly, deflection of the leader 130, such as by the insertion of an insertable instrument 140 within a working channel 139 or through an articulable region 138 of the leader 130, can be detected and/or measured by drive mechanism 500 or component(s) thereof.

Figure 6A:
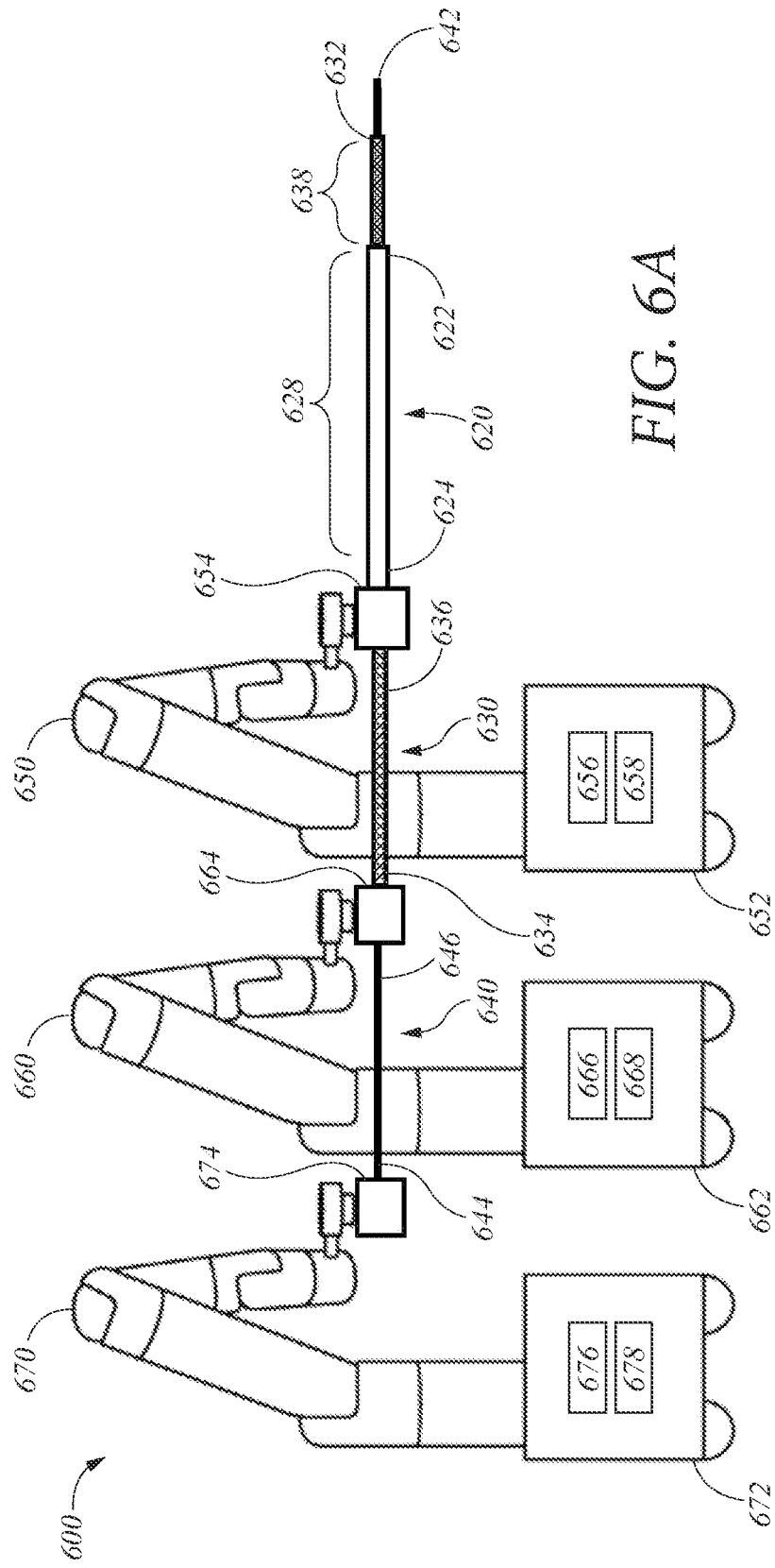
FIG. 6A illustrates another embodiment of a robotic system.

FIG. 6A illustrates an embodiment of a robotic system 600. Similar to the robotic system 100, the system 600 can comprise a sheath 620, a leader 630, and an insertable instrument 640. The leader 630 is configured to be inserted into a lumen of a patient (not shown) and navigated within the luminal network of the patient. For example, the sheath 620 and the leader 630 can have the same or similar structure and mechanics as the sheath 120 and the leader 130 described above, respectively.

The leader 630 can include a distal end 632, a proximal end 634, a shaft 636 extending between the distal end 632 and the proximal end 634, and an articulable region 638 of the shaft 636. The articulable region 638 is configured to be articulated with respect to a shaft 636 to facilitate navigation of the leader 630 through the lumen of the patient after being extended from the distal end 622 of the sheath 620. The distal end 632 can be guided through the lumen of the patient by articulating the articulable region 638 to select a pathway for the distal end 632 and by advancing the shaft 636 and the distal end 632 through the lumen of the patient from the proximal end 634. Similar to the above, the sheath 620 can be advanced along with the leader 630 and provide support thereto, such as for articulating the articulable region 638 and further advancing the leader 630. In this manner, the distal end 632 can be navigated through the lumen of the patient to a target position (e.g., see target position 118 in FIG. 2B). The articulable region 638 is located between the proximal end 634 and the distal end 632, and is adjacent to the distal end 632 in the present example. This arrangement can facilitate the navigation of the leader 630 through the luminal network of the patient. Like the distal end 132 of the leader 130, the leader 130 can include sensors for navigating the lumen of the patient, such as those described in relation to FIGS. 4A-5. Any of the above described tracking systems can be used to track the location of the distal end 632 or detect changes in the location.

Similar to the sheath 120 shown in FIG. 1A, the sheath 620 shown in FIG. 6A can include a distal end 622, a proximal end 624, a shaft 626 extending between the distal end 622 and the proximal end 624, and an articulable region 628 of the shaft 626. The articulable region 628 can be articulated with respect to a shaft 626 to facilitate navigation of the sheath 620 through the lumen of the patient and to provide support to the leader 630.

A proximal portion including the proximal end 624 of the sheath 620 can be supported by a first robotic arm 650 configured to guide or navigate the sheath 620 through the lumen of the patient and coupled with a drive mechanism 654. The first robotic arm 650 and drive mechanism 654 can include structural and functional features similar to the first robotic arm 150 and drive mechanism 154 discussed above in the robotic system 100. The first robotic arm 650 can include a base 652 and multiple arm segments coupled at joints extending from the base 652, a source of power, pneumatic pressure, and control and sensor electronics—including components such as, for example, a central processing unit 656, data bus, control circuitry, and memory 658—and related actuators such as motors to move the first robotic arm 650. The base 652 can include wheels to transport the robotic system 600 and wheel locks/brakes for the wheels. As described further above with respect to FIG. 5, the drive mechanism 654 can also manipulate the tensioning of pull wires to articulate the articulable region 628.

A proximal portion including the proximal end 634 of the leader 630 can be supported by a second robotic arm 660 configured to guide or navigate the leader 630 through the lumen of the shaft 626 of the sheath 620 and into the lumen of the patient. As with the first robotic arm 650, the second robotic arm 660 can include a base 662, multiple arm segments coupled at joints, brakes and/or counter-balances to maintain a position of the second robotic arm 660.

An end effector or a drive mechanism 664 can be coupled with the second robotic arm 660 to control the leader 630. Like the drive mechanisms 154, 164, the drive mechanism 664 can include connectors to the leader 630 and manipulate the positioning of the leader 630. As described further above with respect to FIG. 5, the drive mechanism 664 can also manipulate the tensioning of pull wires to articulate the articulable region 638. The base 662 of the second robotic arm 660, similar to the base 152 of the first robotic arm 150, can include a source of power, pneumatic pressure, and control and sensor electronics, a central processing unit 666, data bus, control circuitry, and memory 668, and related actuators such as motors to move the second robotic arm 660. During procedures, a user may control the second robotic arm 660 using control devices, for example the command center.

Similarly, a proximal end 644 of the insertable instrument 640 can be supported by a third robotic arm 670 and/or an instrument manipulator 674 and configured to guide the insertable instrument 640 and control the insertable instrument 640 to perform the medical procedures. The third robotic arm 670 and instrument manipulator 674 can include structural and functional features similar to the first and second robotic arms 650, 660 and the robotic arms in the robotic system 100. Here, however, the insertable instrument 640 is inserted and guided down the working channel 639 of the leader 630. As with the first robotic arm 650, the third robotic arm 670 can include a base 672, multiple arm segments coupled at joints, brakes and/or counter-balances to maintain a position of the third robotic arm 670. The base 672 of the third robotic arm 670 can include a source of power, pneumatic pressure, and control and sensor electronics—including components such as, for example, a central processing unit 676, data bus, control circuitry, and memory 678—and related actuators such as motors to move the third robotic arm 670. The base 672 of the third robotic arm 670 can include wheels and locks/brakes for the wheels.

Alternatively, the insertable instrument 640 can be configured to operated manually, such as by the physician. In such an embodiment, the insertable instrument 640 can include the EM sensor 482 configured to provide data that can track the location of the insertable instrument 640 within the working channel 629 or into the lumen of the patient, as described above in relation to the EM sensor 482.

The insertable instrument 640 can have various physical characteristics such as a diameter small enough that it can be inserted into the working channel 629, length sufficient to extend through the leader 630, weight, and flexural rigidity along its length. In some embodiments, the insertable instrument 640 comprises an identification tag, the tag corresponding or containing information about the specific insertable instrument 640, and including information such as the instrument's physical properties. In some embodiments, the robotic system 600 can automatically identify the insertable instrument 640 based on the tag. For example, the tag can be an RFID tag, barcode, or the like. In some embodiments, the physical properties associated with the insertable instrument 640 are taken into account by the robotic system 600 to determine an expected deflection response of the leader 630 due to the insertion of the insertable instrument 640 into the leader 630.

In some embodiments, to increase the reach of the system 600 into the lumen of the patient, for example, to gain access to the periphery of a patient's lung, an insertable instrument such as an extended working channel having a smaller diameter than the leader 630 can be inserted into a working channel 639 of the leader 630 and extended out into the lumen of the patient at a distal end 632 of the leader 630. The distal end of the extended working channel can then be extended or navigated to a target position 618, corresponding to a tissue site of the lumen of the patient for implementing the medical procedure. A distal end 642 of the insertable instrument 640 is configured to be inserted through a working channel of the extended working channel and advanced to the distal end thereof and access the tissue site for performing the medical procedures. The extended working channel can thereby increase the access or reach of the leader 130 alone.

In some medical procedures, the size and/or flexibility of the leader 630 or sheath 620 increase the possibility of damage to the lumen of the patients by the passage of the leader 630. Therefore, it may be desirable in some medical procedures to use only the leader 630 without the sheath 620. For example, the leader 630 can be advanced into the lumen of the patient and controlled using the second robotic arm 660. As the leader 630 in such an embodiment may have a larger diameter than the leader 630 used in conjunction with the sheath 620, the leader 630 may be used with or without an extended working channel, such as to gain access to the periphery of a patient's lung.

Figure 6B:
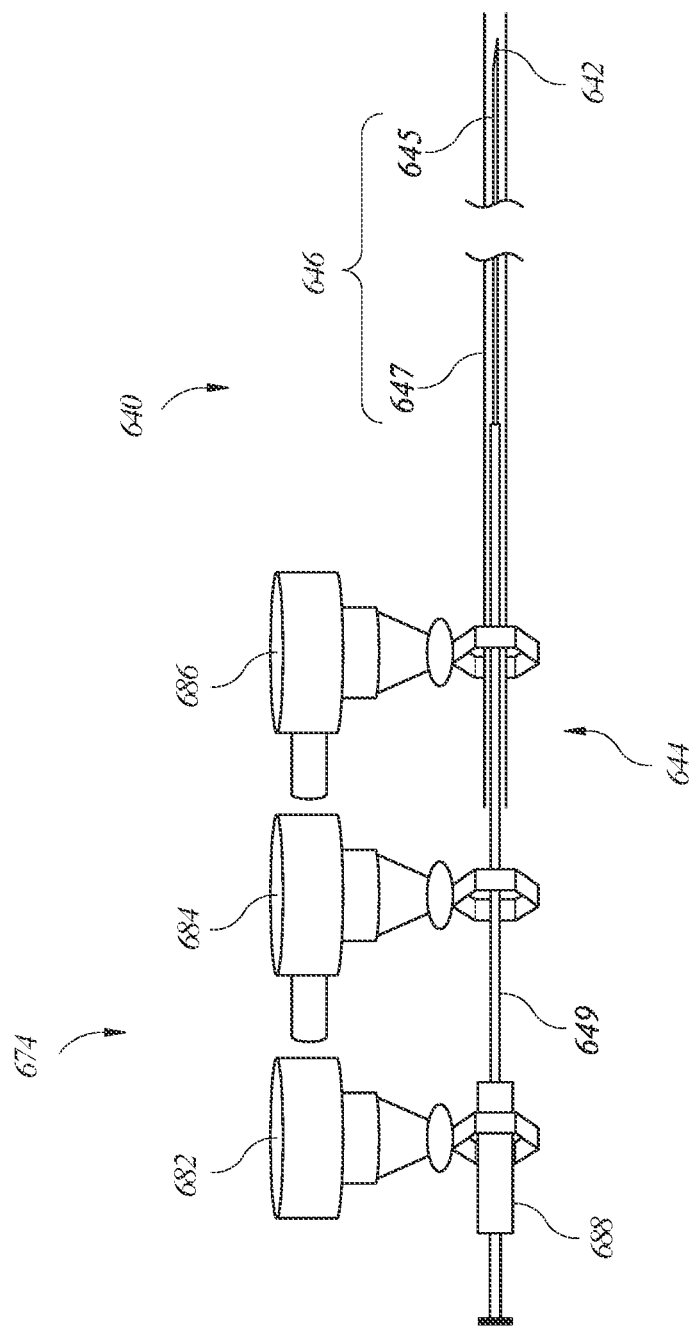
FIG. 6B illustrates an embodiment of an instrument manipulator for controlling an instrument.

FIG. 6B depicts an embodiment of an instrument manipulator configured to control advancement and operation of one or more instruments. Although described below with reference to the robotic system 600 for illustrative purposes, the instrument manipulator 674 as described herein can in some embodiments be used in conjunction with robotic system 100, such as to replace the manual control of the insertable instrument 140. With reference to FIG. 6B, the instrument manipulator 674 can be configured to support the proximal end 644 of the insertable instrument 640 and, in conjunction with the third robotic arm 670. The instrument manipulator 674 and/or robotic arm 670 can navigate the distal end 142 of the insertable instrument 140 through the working channel 639 of the leader 630 to access the tissue site.

In one example, the insertable instrument 640 can be a needle assembly. The needle assembly includes a jacket 647, needle 645, and a tubular elongate shaft 649 connected to the needle. The third robotic arm 670 can be configured to locate, and maintain positioning of, the needle assembly. The third robotic arm 670 may include a first grip portion 682 for controlling and administering therapeutics and two additional grip portions 684, 886 that can secure the shaft 649 and jacket 647, respectively. In some embodiments, the first, second, and third grip portions 682, 684, 686 can be on the same robotic arm, as described above, or on different robotic arms in any combination. The first grip portion 682 can include one or more actuators 688 for controlling, for example, a syringe and/or robotically controlling a plunger of the syringe. The third grip portion 686 may maintain stationary positioning of the jacket 647. The second grip portion 684 can be configured to move the proximal end of the shaft 649 proximally and distally to move the needle 645 in and out of the jacket 647 and/or to effect sampling of the tissue site.

Other examples of instruments include but are not limited to forceps, brushes, scalpels, lasers, augers, cameras, and probes. In some embodiments, the insertable instrument 640 can be substituted for other embodiments of instruments intra-operatively to perform multiple treatments aspects in a single procedure. As another example, the instrument manipulator 674 can include a drive mechanism having at least one pull wire, similar to drive mechanisms described herein, such as for actuating forceps using the at least one pull wires.

In other examples, the instrument manipulator can include various motors, pressure regulators, electrical connections, etc. for operating the insertable instrument 640 to perform various medical procedures. Thus, the instrument manipulator 674 can have various configurations to accommodate a variety of instrument types.

FIG. 7 illustrates the command center 700 that can be used, for example, in conjunction with the robotic systems described above. The command center 700 includes a console base 701, display modules 702, e.g., monitors, and control modules, e.g., a keyboard 703 and joystick 704. In some embodiments, one or more of the command center 700 functionalities may be integrated into the controller on the robotic system or another system communicatively coupled to the robotic system. A user 705, e.g., a physician, may remotely control the robotic system from an ergonomic position using the command center 700.

The console base 701 may include a central processing unit, a memory unit, a data bus, and associated data communication ports that are responsible for interpreting and processing signals such as data from any of the tracking systems described above including but not limited to: the tension sensing system, the optical tracking system, the inertial tracking system, the EM tracking system, and the physiological tracking system.

The console base 701 can also process commands and instructions provided by the user 705 through the control modules 703 and 704. In addition to the keyboard 703 and joystick 704 shown in FIG. 7, the control modules may include other devices, for example, computer mice, trackpads, trackballs, control pads, system controllers such as handheld remote controllers, and sensors (e.g., motion sensors or cameras) that capture hand gestures and finger gestures. A system controller can include a set of user inputs (e.g., buttons, joysticks, directional pads, etc.) mapped to an operation of the instrument (e.g., articulation, driving, water irrigation, etc.).

The user 705 can control a flexible instrument (e.g., the sheath 120, leader 130, sheath 620, or leader 630, although described herein in terms of the leader 130) using the command center 700 in, for example, a velocity mode or position control mode. In velocity mode, the user 705 directly controls pitch and yaw motion of a distal end 132 of the leader 130 based on direct manual control using the control modules. For example, movement on the joystick 704 may be mapped to yaw and pitch movement in the distal end 132 of the leader 130. The joystick 704 can provide haptic feedback to the user 705. For example, the joystick 704 may vibrate to indicate that the leader 130 cannot further translate or rotate in a certain direction. The command center 700 can also provide visual feedback (e.g., pop-up messages) and/or audio feedback (e.g., beeping) to indicate that the leader 130 has reached maximum translation or rotation. The haptic and/or visual feedback can also be provided due to the system operating in a safety mode during patient expiration as described in more detail below.

In position control mode, the command center 700 can use a three-dimensional (3D) map of a patient lumen and input from navigational sensors as described herein to control a surgical instrument, e.g., the leader 130. The command center 600 provides control signals to robotic arms of the robotic system 100 to manipulate the distal ends 122 (or distal end 632) to the target position 118, such as by control of the articulation angle 116 of the articulable regions 128.

In some embodiments, a model of the leader 130 is displayed with the 3D models to help indicate a status of a surgical procedure. For example, the CT scans identify a lesion in the anatomy where a biopsy may be necessary. During operation, the display modules 702 may show a reference image captured by the leader 130 corresponding to the current location of the leader 130. The display modules 702 may automatically display different views of the model of the leader 130 depending on user settings and a particular surgical procedure. For example, the display modules 702 show an overhead fluoroscopic view of the leader 130 during a navigation step as the leader 130 approaches an operative region of a patient.

Example Deflection Compensation Techniques

Figure 8:
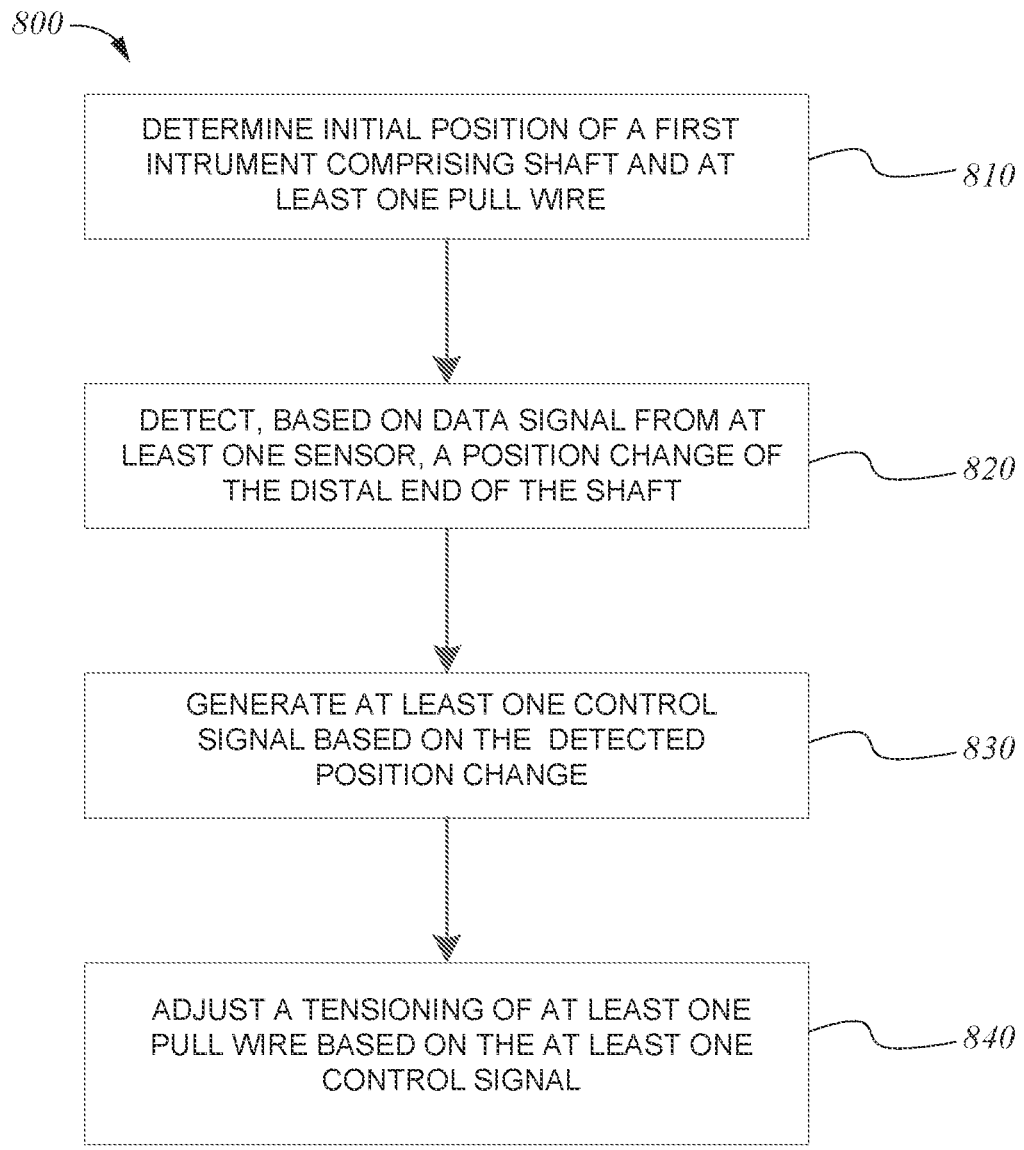
FIG. 8 is a flowchart of an example methodology of tracking and compensating for deflection of a flexible instrument.

In accordance with one or more aspects of the present disclosure, FIG. 8 depicts a flowchart of an implementation of a tracking compensation process 800 for detecting and compensating for a deflection of the distal end of a flexible instrument. The process 800 is described with reference to the robotic system 100 for illustrative purposes; however, the process 800 may be implemented on other suitable robotic systems.

The process 800 can begin based on conditions of and/or inputs into the robotic system 100. For example, process 800 can begin based on or in response to the position of a first instrument, e.g., the insertable instrument 140 within the working channel 139 of the leader 130. For example, the process 800 can begin based on a specific position of the distal end 142 of the insertable instrument 140 within the working channel 139, such as proximity to an articulable region 138 of the leader 130 (e.g., within about 10 cm) or the distal end 132 of the leader 132. In another example, the system 100 can determine that the user is manually triggering the process 800 through a user interface or user input device, such as at the command center 700. In yet another example, the process 800 can be triggered automatically as the system 100 recognizes that the distal end 132 of the leader 130 has been navigated to the target position 118 using one of the above-described tracking systems. In still another example, the process 800 is initiated in response to there being no further user inputs or commands to move or manipulate any of the controllable elements of the system 100.

At block 810, the system 100 can determine (e.g., detect or measure) an initial position of a first instrument. The first instrument may comprise: a shaft comprising proximal and distal portions, the distal portion comprising an articulable region and a distal end, the shaft comprising a working channel extending therethrough; and at least one pull wire. Block 810 may involve determining an initial position of a distal end of a flexible instrument (e.g., distal end 132 of the leader 130). In some implementations, the initial position can correspond to the target position 118.

Any of the above-described tracking systems for monitoring the position of the distal end 132 can be used to detect the initial position of the distal end 132. For example, the EM tracking system 480 can relay data about the sensor 484 to the controller indicating the initial position of the distal end 132; and/or the inertial tracking system can relay data about the sensor 460 indicating the initial position of the distal end 132. The electrical strain gauges 554 can relay data based on the tensioning of the pull wire(s) 556 indicating the initial position of the distal end 132. The camera 450 of the optical tracking system can relay data based on optical positioning indicating the initial position of the distal end 132.

At block 820, the system 100 can detect, based on a data signal from at least one sensor, a position change (e.g., deflection) of the distal end of the shaft in response to insertion of a second instrument into the working channel of the first instrument. For example, block 820 may involve detecting, based on a data signal from at least one sensor, a position change of the distal end 132 of the leader 130 from the initial position, e.g., in response to insertion of an insertable instrument 140 into a working channel 139 of the leader 130. Any of the above-described tracking systems for monitoring the position of the distal end 132 can be used to detect the deflection of the distal end 132. The controller can receive data indicating a deflection from the tension sensing system, the optical tracking system, the inertial tracking system, and/or the EM tracking system 480. For example, the EM tracking system 480 can relay data about the sensor 484 indicating a change in the position of the distal end 132 to the controller; the inertial tracking system can relay data about the sensor 460 indicating a change in the position of the distal end 132 and/or the deflected position 119 to the controller; the optical tracking system can relay data from the camera 450 indicating a change in the position of the distal end 132 to the controller; and/or the tension sensing system 500 can relay data from the strain sensors 554 indicating a change in the articulation angle 116 of the articulable region 138 to the controller.

In some examples, measuring the position change can involve filtering out physiological movement (e.g., the respiration pattern) of the patient that is different from and/or not indicative of the deflection of the distal end 132 (e.g., changes in the articulation angle 116). For example, at, before, or after block 820 in the process 800, a data signal from the physical physiological movement sensors 490 can be received by the controller. The system 100 can thus take into account (e.g., compensate for) detected position changes of the distal end 132 due to physiological movement of the patient.

At block 830, the system 100 can generate at least one control signal based on the detected position change of the distal end of the shaft. For example, block 830 may involve generating at least one control signal based on the data from the tracking system indicating the position change of the distal end 132. The generated control signal can be at least partially based on the initial position, the magnitude, direction and/or angle of any detected deflection, and/or the signal from the physiological movement sensors 490.

The control signal can include instructions for returning the distal end 132 back to an initial position. In some embodiments, the control signal can include instructions for returning the distal end 132 back to the target position 118. For example, the control signal can include instructions for the drive mechanism 164 to adjust a tensioning of at least one of the pull wires 556 of the leader 130 to compensate for the deflection and thereby return the distal end 132 back to the initial position. In the alternative, or in addition, the control signal can include instructions for the drive mechanism 154 to adjust a tensioning of at least one of the pull wires of the sheath 120 to return the distal end 132 of the leader 130 back to its initial position.

A block 840, the system 100 can adjust a tensioning of the at least one pull wire based on the at least one control signal, wherein the adjusted tensioning facilitates returning the distal end of the shaft to the initial position. For example, block 840 may involve adjusting a tensioning of at least one pull wire of the leader 130 and/or sheath 120 based on the at least one control signal. For example, the drive mechanism 164 and/or drive mechanism 154 can execute the instructions in the control signal and adjust a tensioning of one or more pull wires (of the leader 130 and/or the sheath 120) to return the distal end 132 to the initial position, and thereby compensate for any deflection of the distal end 132 due to the insertion of the insertable instrument 140.

The system 100 can end the process 800 based on any of several conditions. In one example, the system 100 ends the process 800 upon detecting that the distal end 132 of the leader 130 has returned to the initial position after the detected position change. In another example, the system 100 ends the process 800 in response to receiving an overriding input control signal from the user, for example, via the command center 700. In another example, the system 100 ends the process 800 based on detecting a manual input by the user. In another example, the process 800 can be ended by the position and/or direction of movement (e.g., retraction) of the insertable instrument 140 within the working channel 139 of the leader 130. For example, a movement detected by the EM tracking system 480 can indicate retraction of the insertable instrument 140 from the articulable region 138 and/or from the working channel 139.

Alternatively, having detected one deflection of the distal end 132 from the initial position, the process 800 can be repeated as the position of the distal end 132 continues to be tracked or monitored by the system 100. Subsequent detections of deflection of the distal end 132, generating control signals, and adjusting of tensioning of the pull wires 556 of the leader 130 and/or sheath 120 can be continued as outlined above.

In another implementation, the process 800 described above can be performed using the robotic system 600 and by detecting deflection of the distal end 632 of the leader 630. At block 810, the system 600 can detect an initial position (e.g., target position 618) of the distal end 632 of the leader 630 using any of the above-described tracking systems. At block 820, the system 600 can detect a position change (e.g., deflection) of the distal end 632 of the leader 630, such as, for example, by using the tension sensing system or the EM tracking system 480, and/or any other tracking systems described herein. In the alternative, or in addition, any of the above-described tracking systems can be used to detect the deflection of the distal end 622 of the sheath 620—which can also be indicative of a deflection of the distal end 632 of the leader 630 requiring compensation.

At block 830, the system 600 can generate at least one control signal based on the data from the tracking system indicating the position change, the detected deflection, the physiological movement sensors 490, and/or the magnitude of the deflection. The control signal can include instructions for returning the distal end 632 back to the initial position (e.g., instructions for the drive mechanism 664 to adjust a tensioning of at least one of the pull wires 556 of the leader 630). In the alternative, or in addition, the control signal can include instructions for the drive mechanism 654 to adjust a tensioning of at least one of the pull wires of the sheath 620 to return the distal end 632 of the leader 630 back to its initial position.

A block 840, the drive mechanism 664 and/or drive mechanism 654 can execute the instructions in the control signal and adjust a tensioning of one or more pull wires of the leader 630 and/or the sheath 620 to return the distal end 632 of the leader 630 to the initial position.

Figure 9:
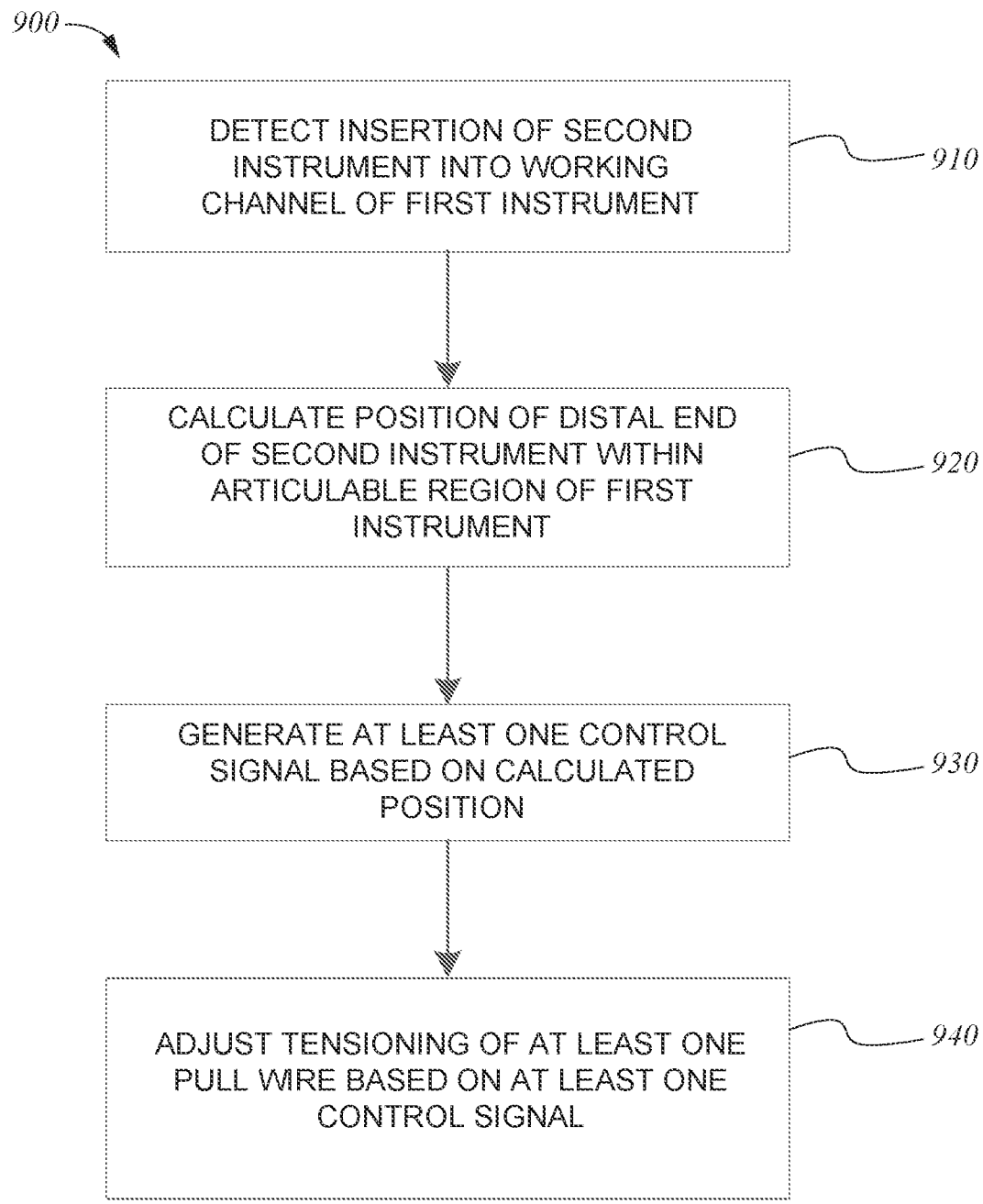
FIG. 9 is a flowchart of an example methodology of predicting and compensating for deflection of a flexible instrument.

In accordance with one or more aspects of the present disclosure, FIG. 9 depicts a flowchart of an example process for compensating for deflection of a first instrument, e.g., a flexible instrument, based on controlling at least one pull wire of the first instrument. The process 900 is described with reference to the robotic system 100 for illustrative purposes; however, the process 900 may be implemented on other suitable robotic systems.

The process 900 can begin based on any of several conditions or inputs to the system 100. At block 910, the system 100 can detect insertion of a second instrument into a working channel of the first instrument, wherein the second instrument may comprise proximal and distal ends. The first instrument may comprise: a shaft comprising proximal and distal portions, the distal portion comprising an articulable region; and at least one pull wire. The condition can be based on the position of the insertable instrument 140 (e.g., a specific position of the distal end 142 of the insertable instrument 140) within the working channel 139 of the leader 130, such as the proximity of the insertable instrument 140 to an articulable region 138 or distal end 132 of the leader 130 (e.g., within about 2 cm, 5 cm, 10 cm, or any other suitable threshold distance). Additionally or alternatively, the system 100 can determine that the user is manually triggering the beginning of the process 900 through a user interface, such as at the command center 700. In one example, the process 900 can be initiated automatically as the system 100 recognizes that the distal end 132 is in the target position 118 (e.g., based on the system 100 automatically detecting this condition and/or based on the system 100 receiving a user input indicative of this condition). In yet another example, the process 900 is initiated in response to there being no further user inputs or commands to move or manipulate any of the controllable elements of the system 100.

In one embodiment, the system 100 can track the advancement of the insertable instrument 140 through the working channel 139. For example, the EM tracking system 480 can relay data about the sensor 482 of the insertable instrument 140 to the controller indicating the position of the distal end 142 within the working channel 139. The position with the working channel 130 can include the proximity to and/or arrival of the distal end 142 at the articulable region 138 and/or at the distal end 132 of the leader 130.

At block 920, the system 100 can calculate a position of the distal end of the second instrument within the articulable region. For example, block 920 may involve calculating the position of the distal end of the second instrument within the articulable region based on data from the EM tracking system 480 and/or robot control data.

At block 930, the system 100 can generate at least one control signal based on the calculated position of the distal end of the second instrument within the articulable region. In other embodiments, the at least one control signal may be based on the predicted deflection of the first instrument resulting from the calculated position of the distal end of the second instrument within the articulable region. The control signal can include instructions for preventing the distal end 132 from deflecting from the target position 118 or otherwise returning the distal end 132 at the target position based on the predicted deflection. For example, the control signal can include instructions for the drive mechanism 164 to adjust a tensioning of at least one of the pull wires 556 of the leader 130 to prevent or minimize any deflection that may otherwise occur. In some embodiments, the control signal can include instructions for the drive mechanism 154 (or both drive mechanisms 154, 164) to adjust a tensioning of at least one of the pull wires to maintain the distal end 132 at the target position 118. It is to be appreciated that in some cases the leader may compress as a result of the increased tensioning on the pull wires. In such cases, the control signal may also instruct a robotic arm controlling the leader to cause the leader to be inserted a specified distance that is related to the compression that will be experienced by the leader. In this way, the combination of the insertion and the compression along the length of the leader is such that the distal end of the leader maintains its location within the anatomy (e.g., the target position 118).

At block 940, the drive mechanism 500 of the system 100 can adjust a tensioning of the at least one pull wire based on the at least one control signal, wherein the adjusted tensioning facilitates maintaining a position of the distal portion of the shaft. For example, block 940 may involve executing instructions in the control signal and adjusting the tensioning of the pull wire(s) 556 of the leader 130. In some embodiments, the instructions contained in the control signal are executed in coordination with a determinable position of the distal end 142 of the insertable instrument 140 within the working channel 139. For example, the determinable position can be calculated using the data from the EM sensor 482 on the insertable instrument 140. In other implementations of the method, such as using system 600 described above, the determinable position can be calculated based on the known positions of the robotic arms and their relations to one another. In some implementations, the instructions of the control signal are executed before the distal end 142 of the insertable instrument 140 is inserted to a particular determinable position, such as within the articulable region 138. In such a preemptive model or approach, the distal end 132 may be temporarily deflected out of the target position 118 by the control signal, but the distal end 132 returns to the target position 118 once the insertable instrument 140 is advanced to a second determinable position, such as the articulable region 138 or the distal end 132. In another embodiment, the instructions of the control signal can be executed after the distal end 142 of the insertable instrument 140 is advanced to the distal end 132 or through the articulable region 138. In such a model or approach, the distal end 132 is temporarily deflected and then returned to the target position 118 after the control signal is fully executed.

In another example of the preemptive approach, system 100 minimizes the extent or magnitude of deflection of the distal end 132 from the target position by executing the control signal in coordination with the determinable position of the distal end 142 of the insertable instrument 140 (e.g., substantially concurrently), thereby minimizing the amount of deflection experienced by the distal end 132. For example, the control signal can be executed to adjust the tensioning of the one or more pull wires in increments as the distal end 142 of the insertable instrument is advanced through the articulable region 138.

The end of the process 900 can be triggered by an overriding input control signal from the user or the command center 700 or another component of the system 100. In one example, the end of the process 900 can also be triggered by the system 100 receiving a manual input by the user. In another example, the end of the process 900 can be triggered by automatic detection of a position of the distal end 142 of the insertable instrument 140 within the working channel 139, such as a positional indication that the insertable instrument 140 is being retracted from the working channel or has been retracted from the articulable regions 138.

In accordance with one or more aspects, there is a provided a process that involves calculating a predicted deflection of the first instrument, e.g., the distal end 132 from target position 118 due to the insertion of the insertable instrument 140 through the articulable region 138. The calculated predicted deflection can be based on one or more factors such as, for example, the location of the insertable instrument 140 within the working channel 139, the location of the instrument relative to an articulable region 138 of the leader 130, and/or the articulation angle 116 of the articulable region 138. The calculated predicted deflection can also be based on, for example, the physical properties of the leader 130 and/or the insertable instrument 140 (including pull wires thereof), such as, length, diameter, weight, elasticity, and/or flexural rigidity, etc.

In some embodiments, the system 100 calculates the predicted deflection by recognizing the insertable instrument 140 and/or correlating it with known physical characteristics of the insertable instrument 140. For example, the insertable instrument 140 can be identified based on its tag, such as an RFID tag that can include information (e.g., physical properties) about that particular instrument. The insertable instrument 140 can be correlated to a set of physical properties of the instrument such as, for example, the instrument diameter, length, weight, and/or flexural rigidity of specific portions of the insertable instrument 140. This information can be taken into consideration by the system 100 when calculating the predicted deflection. In some embodiments, the location of the distal end 142 of the insertable instrument 140 is taken into account in calculating the compensation based on data from the EM sensor 482 used in conjunction with the EM tracking system 480.

In some embodiments, the predicted deflection may be calculated by a controller or computing device communicatively coupled with the system 100 using the factors and physical properties described above and a predictive, mathematical model of the leader 130 and/or insertable instrument 140. In other embodiments, the predicted deflection is known/stored in memory or looked up in a database. In such an embodiment, the appropriate control signal and/or predicted deflection can be looked up in a corresponding database based on information about the system 100 (e.g., physical properties of the leader 130 or insertable instrument 140, articulation angle 116, tension in the one or more pull wires 554, or other properties of the system 100). For example, given a known articulation angle 116 of the articulable region 138, a known leader 130, and a known insertable instrument 140, the predicted deflection can be looked up in a database correlating these variables.

Alternatively, having calculated one predicted deflection of the distal end 132, the above process 900 can be repeated as the position of the insertable instrument 140 continues to be tracked or monitored by the system 100. Subsequent calculations predicting the deflection of the distal end 132 can be processed as outlined above until the end of the process 900.

In another implementation, the process 900 described above can be performed using the robotic system 600 and by predicting deflection of the distal end 632 of the leader 630. At block 910, the system 600 tracks the position of the insertable instrument 640 within the working channel 639 based on the position, models, sensors, and/or controls of the system 600. For example, the system 600 can track the position of the insertable instrument 640 based on the robotic insertion data of the robotic arms 650, 660, and/or 670 which guide and support the sheath 620, leader 630, and/or insertable instrument 640, respectively. This robotic insertion data can, for example, include data indicating the position and orientation of the distal end 642 of the insertable instrument 640 relative to the articulable region 638 and/or distal end 632 of the leader 630, for example, as the distal end 642 advances through the working channel 639.

At block 920, the system 600 can calculate a predicted position change or deflection of the distal end 632 of the leader 630 from the target position 618 based at least in part on the pose of the first instrument, or component(s) thereof.

For example, the system 600 can calculate the predicted position change based on the position and orientation of the leader 630 and/or sheath 620 (e.g., articulation angle 616 and/or tension in the pull wire 556). In another example, the system 600 can calculate (or lookup in a database) the predicted position change based on one or more of the physical properties of the system, such as the physical properties of the leader 630 and/or insertable instrument 640 (e.g., flexural rigidity of the insertable instrument 640 and/or flexural rigidity of the articulable region 638 of the leader 630), which in some examples may be coded into an RFID tag or the like on the leader 630 and/or insertable instrument 640 (read by an RFID reader or scanner, e.g., of the system 600).

At block 930, the system 600 can generate a control signal based on the predicted deflection. The control signal can include instructions for returning the distal end 632 back to the target position 618. In some embodiments, the control signal can include instructions for the drive mechanism 654 (or both drive mechanisms 654 and 664) to adjust a tensioning of at least one of the pull wires 556 to compensate for the predicted deflection and thereby return the distal end 632 back to the target position 618.

At block 940, the drive mechanism 500 of the system 600 can execute the instructions in the control signal and adjust a tensioning of one or more pull wires 556. In some embodiments, the instructions contained in the control signal are executed in coordination with a determinable position of the distal end 642 of the insertable instrument 640 within the working channel 639. For example, the control signal can be executed before the distal end 642 is advanced to the determinable position, the control signal can be executed after the distal end 642 is advanced to the determinable position, or the control signal can be executed concurrently (e.g., incrementally) with the advancement of the distal end 642 through the working channel 639 of the leader 630.

Further Implementations

In accordance with one or more aspects, there is provided a robotic system that comprises: a first instrument that comprises (i) a shaft comprising a proximal portion and a distal portion, the distal portion comprising an articulable region, the shaft comprising a working channel extending therethrough, (ii) and at least one pull wire. The robotic system may further comprise at least one sensor configured to detect, in response to insertion of a second instrument into the working channel, a position of a distal end of the second instrument within the working channel. The robotic system may further comprise at least one computer-readable memory having stored thereon executable instructions, and one or more processors in communication with the at least one computer-readable memory and configured to execute the instructions to cause the system to at least: calculate, based on a data signal from the at least one sensor, the position of the distal end of the second instrument within the working channel; and generate at least one control signal based on the calculated position. The robotic system may further comprise a drive mechanism connected to the at least one pull wire at the proximal portion of the shaft, the drive mechanism configured to use a tensioning of the at least one pull wire based on the at least one control signal, wherein the adjusted tensioning facilitates maintaining a position of the distal portion of the shaft.

In related aspects, the drive mechanism may be configured to use the tensioning of the at least one pull wire: as the distal end of the second instrument advances to a determinable position in relation to the articulable region; before the distal end of the second instrument advances to the determinable position; and/or after the distal end of the second instrument advances to the determinable position.

In further related aspects, the one or more processors may be configured to execute the instructions to cause the system to: detect an identifier on the second instrument; and generate the at least one control signal further based on the detected identifier.

In still related aspects, the one or more processors are configured to execute the instructions to cause the system to determine at least one physical property of the second instrument based on the detected identifier, wherein: the at least one physical property of the second instrument comprises a flexural rigidity value; and the one or more processors are configured to execute the instructions to cause the system to generate the at least one control signal further based on the flexural rigidity value.

In yet further related aspects, the one or more processors are configured to execute the instructions to cause the system to: determine an articulation angle of the articulable region of the shaft; and generate the at least one control signal further based on the articulation angle.

In additionally related aspects, the one or more processors are configured to execute the instructions to cause the system to detect the identifier based on reading an RFID tag of the second instrument.

In related aspects, the robotic system may further comprise an EM field generator, wherein: the at least one sensor comprises a set of one or more EM sensors at the distal end of the second instrument; and the one or more processors are configured to execute the instructions to cause the system to calculate a position of the set of EM sensors within the EM field based on data from the set of EM sensors, and calculate the positon of the distal end of the second instrument within the working channel further based on the calculated position of the set of EM sensors.

In accordance with one or more aspects, there is provided a method of controlling at least one pull wire of a first instrument, the method comprising: detecting insertion of a second instrument into a working channel of the first instrument, the second instrument comprising proximal and distal ends, the first instrument, comprising a shaft comprising proximal and distal portions, the distal portion comprising an articulable region, and the at least one pull wire; calculating a position of the distal end of the second instrument within the articulable region; generating at least one control signal based on the calculated position; and adjusting a tensioning of the at least one pull wire based on the at least one control signal, wherein the adjusted tensioning facilitates maintaining a position of the distal portion of the shaft.

In related aspects, the method may further comprise adjusting the tensioning of the at least one pull wire: as the distal end of the second instrument advances to a determinable position in relation to the articulable region; before the distal end of the second instrument advances to the determinable position; and/or after the distal end of the second instrument advances to the determinable position.

In further related aspects, the method may further comprise: detecting an identifier on the second instrument; and generating the at least one control signal further based on the detected identifier.

In yet further related aspects, the method may further comprise determining at least one physical property of the second instrument based on the detected identifier, wherein the at least one control signal is generated further based on the at least one physical property. The at least one physical property may comprise a flexural rigidity value of the second instrument. The detecting of the identifier may comprise reading an RFID tag of the second instrument.

In still further related aspects, the calculated position of the distal end of the second instrument within the articulable region may be based on data from at least one EM sensor on the distal end of the first instrument.

In accordance with one or more aspects, there is provided a non-transitory computer readable storage medium having stored thereon instructions that, when executed, cause at least one computing device to at least, for a first instrument comprising at least one pull wire and an articulable region: detect insertion of a second instrument into a working channel of the first instrument; calculate a position of a distal end of the second instrument within the articulable region; generate at least one control signal based on the calculated position; and adjust a tensioning of the at least one pull wire based on the at least one control signal, wherein the adjusted tensioning facilitates maintaining a position of the distal portion of the first instrument.

In related aspects, the instructions that cause the at least one computing device to adjust the tensioning may cause the at least one computing device to adjust the tensioning of the at least one pull wire as the distal end of the second instrument advances to a determinable position in relation to the articulable region.

In further related aspects, the instructions that cause the at least one computing device to adjust the tensioning may cause the at least one computing device to adjust the tensioning of the at least one pull wire before the distal end of the second instrument advances to the determinable position.

In yet further related aspects, the instructions that cause the at least one computing device to adjust the tensioning may cause the at least one computing device to adjust the tensioning of the at least one pull wire after the distal end of the second instrument advances to the determinable position.

In still further related aspects, the instructions that cause the at least one computing device to adjust the tensioning may cause the at least one computing device to: detect an identifier on the second instrument; and generate the at least one control signal further based on the detected identifier.

In additionally related aspects, the instructions that cause the at least one computing device to adjust the tensioning may cause the at least one computing device to determine at least one physical property of the second instrument based on the detected identifier, wherein the at least one control signal is generated further based on the at least one physical property. The at least one physical property may comprise a flexural rigidity value of the second instrument.

Implementing Systems and Terminology

Implementations disclosed herein provide systems, techniques and apparatus for improved navigation of lumens.

It should be noted that the terms "couple." "coupling." "coupled" or other variations of the word couple as used herein can indicate either an indirect connection or a direct connection. For example, if a first component is "coupled" to a second component, the first component can be either indirectly connected to the second component via another component or directly connected to the second component.

The automatic compensation functions described herein can be stored as one or more instructions on a processor-readable or computer-readable medium. The term "computer-readable medium" refers to any available medium that can be accessed by a computer or processor. By way of example, and not limitation, such a medium can comprise RAM (random-access memory), ROM (read-only memory), EEPROM (electrically erasable programmable read-only memory), flash memory, CD-ROM (compact disc read-only) or other optical disk storage, magnetic disk storage or other magnetic storage devices, or any other medium that can be used to store desired program code in the form of instructions or data structures and that can be accessed by a computer. It should be noted that a computer-readable medium can be tangible and non-transitory. As used herein, the term "code" can refer to software, instructions, code or data that is/are executable by a computing device or processor.

The techniques disclosed herein comprise one or more steps or actions for achieving the described method. The method steps and/or actions can be interchanged with one another without departing from the scope of the Alternatives. In other words, unless a specific order of steps or actions is required for proper operation of the method that is being described, the order and/or use of specific steps and/or actions can be modified without departing from the scope of the Alternatives.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present disclosure. Various modifications to these implementations will be readily apparent to those skilled in the art, and the generic principles defined herein can be applied to other implementations without departing from the scope of the disclosure. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present disclosure is not intended to be limited to the implementations shown herein but is to be accorded the widest scope consistent with the principles and novel features disclosed herein.

What is claimed is:

1. A method of controlling an instrument, the method comprising:
   determining a position of a second instrument within a working channel of a shaft of a first instrument;
   in response to determining the position of the second instrument, predict a position change of a distal end of the shaft that would be caused by further advancement of the second instrument within the working channel of the first instrument; and
   generating at least one control signal based on the predicted position change of the distal end of the shaft to control articulation of the first instrument to compensate for the further advancement of the second instrument within the working channel of the first instrument.

2. The method of claim 1, further comprising:
prior to determining the position of the second instrument, controlling the first instrument to a target position;
wherein the at least one control signal prevents the distal end of the shaft of the first instrument from deflecting from the target position when the second instrument is advanced within an articulable region of the working channel of the first instrument.

3. The method of claim 1, further comprising:
prior to determining the position of the second instrument, controlling the first instrument to a target position;
wherein the at least one control signal reduces an amount of deflection of the distal end of the shaft of the first instrument from the target position when the second instrument is further advanced within the working channel.

4. The method of claim 1, further comprising determining a proximity of the second instrument to an articulable region of the first instrument, wherein predicting the position change is performed in response to the determined proximity.

5. The method of claim 1, wherein determining the position change is based on data received from one or more electromagnetic (EM) sensors, one or more inertial sensors, or one or more cameras, associated with the distal end of the shaft.

6. The method of claim 1, further comprising:
determining, based on data from at least one respiration sensor, a respiration pattern; and
distinguishing a position change of the distal end of the shaft caused by the further advancement of the second instrument within the working channel from a position change of the distal end of the shaft caused by the respiration pattern.

7. A non-transitory computer readable storage medium having stored thereon instructions that, when executed, cause at least one computing device to at least:
determine a target position of a distal end of a first instrument;
determine a position of a second instrument within a working channel of the first instrument;
in response to the position of the second instrument, predict a position change of the distal end of the first instrument that would be caused by further insertion of the second instrument within the working channel of the first instrument; and
adjust a tensioning of at least one pull wire associated with the first instrument to compensate for the further insertion of the second instrument within the working channel of the first instrument.

8. The non-transitory computer readable storage medium of claim 7, wherein said adjusting the tension of the at least one pull wire prevents the distal end of the first instrument from deflecting from the target position when the second instrument is inserted within an articulable region of the working channel.

9. The non-transitory computer readable storage medium of claim 7, wherein said adjusting the tension of the at least one pull wire reduces an amount of deflection of the distal end of the first instrument from the target position when the second instrument is further inserted within the working channel.

10. The non-transitory computer readable storage medium of claim 7, wherein the instructions, when executed, further cause the at least one computing device to at least determine a proximity of the second instrument to an articulable region of the first instrument, wherein predicting the position change is in response to the determined proximity.

11. The non-transitory computer readable storage medium of claim 7, wherein predicting the position change is based on data from one or more cameras associated with the distal end of the first instrument.

12. The non-transitory computer readable storage medium of claim 7, having further stored thereon instructions that, when executed, cause the at least one computing device to:
determine, based on data from at least one respiration sensor, a respiration pattern of a patient; and
distinguish a position change of the distal end of the first instrument caused by the further insertion of the second instrument within the working channel from a position change of the distal end of the first instrument caused by the respiration pattern of the patient.

13. A method of controlling an instrument, the method comprising:
determining a first position of a distal end of an endoscope, the endoscope comprising a working channel and one or more pull wires;
determining a position of a working instrument within the working channel of the endoscope;
predicting a second position of the distal end of the endoscope resulting from a position change that would occur in response to further advancement of the working instrument within the working channel of the endoscope; and
in response to said predicting the second position, commanding articulation of the endoscope to compensate for the further advancement of the working instrument within the working channel of the endoscope.

14. The method of claim 13, wherein said commanding articulation of the endoscope prevents the distal end of the endoscope from deflecting from the first position when the working instrument is further advanced within the working channel of the endoscope.

15. The method of claim 13, wherein said commanding articulation of the endoscope reduces an amount of deflection of the distal end of the endoscope from the first position when the working instrument is further advanced within the working channel of the endoscope.

16. The method of claim 13, further comprising determining a proximity of the working instrument to an articulable region of the endoscope, wherein said predicting the second position of the distal end of the endoscope is performed in response to the determined proximity.

17. The method of claim 13, wherein said predicting the second position of the distal end of the endoscope is performed in response to detecting the working instrument within an articulable region of the endoscope.

18. The method of claim 13, further comprising determining, based on data from at least one respiration sensor, a respiration pattern, wherein said predicting the second position of the distal end of the endoscope compensates for the respiration pattern.

19. The method of claim 13, further comprising tracking displacement of the distal end of the endoscope caused by respiration of a patient in which the distal end of the endoscope is disposed.

20. The method of claim 19, further comprising filtering out noise caused by the respiration of the patient when predicting the second position of the distal end of the endoscope.

* * * * *